US007736672B2

(12) United States Patent
Ray et al.

(10) Patent No.: US 7,736,672 B2
(45) Date of Patent: Jun. 15, 2010

(54) MULTIPARTICULATE COMPOSITIONS WITH IMPROVED STABILITY

(75) Inventors: Roderick J. Ray, Bend, OR (US); Leah E. Appel, Bend, OR (US); Dwayne Thomas Friesen, Bend, OR (US); Marshall D. Crew, Bend, OR (US); Joshua R. Shockey, Bend, OR (US)

(73) Assignee: Pfizer, Inc., New York, NY (US)

( * ) Notice: Subject to any disclaimer, the term of this patent is extended or adjusted under 35 U.S.C. 154(b) by 1152 days.

(21) Appl. No.: 11/003,664

(22) Filed: Dec. 3, 2004

(65) Prior Publication Data
US 2005/0186285 A1 Aug. 25, 2005

Related U.S. Application Data

(60) Provisional application No. 60/527,245, filed on Dec. 4, 2003.

(51) Int. Cl.
A61K 9/14 (2006.01)
(52) U.S. Cl. ...................................... 424/489
(58) Field of Classification Search .................. None
See application file for complete search history.

(56) References Cited

U.S. PATENT DOCUMENTS

| 2,955,956 A | 10/1960 | Baugh et al. ............... 117/100 |
| 4,053,264 A | 10/1977 | King ............................ 425/8 |
| 4,086,346 A | 4/1978 | Bocker et al. ............... 424/253 |
| 4,092,089 A | 5/1978 | Bocker et al. ............... 425/10 |
| 4,293,570 A | 10/1981 | Vadasz ......................... 426/3 |
| 4,474,768 A | 10/1984 | Bright ......................... 424/180 |
| 4,517,359 A | 5/1985 | Kobrehel et al. ............ 536/7.4 |
| 4,675,140 A | 6/1987 | Sparks et al. ................ 264/4.3 |
| 4,874,611 A | 10/1989 | Wilson et al. ............... 424/410 |
| 4,931,285 A | 6/1990 | Edgren et al. ............... 424/473 |
| 4,957,681 A | 9/1990 | Klimesch et al. ........ 264/211.23 |
| 4,963,531 A | 10/1990 | Remington .................. 514/29 |
| 5,019,302 A | 5/1991 | Sparks et al. ................. 264/8 |
| 5,024,842 A | 6/1991 | Edgren et al. ............... 424/473 |
| 5,047,244 A | 9/1991 | Sanvordeker et al. ........ 424/435 |
| 5,064,650 A | 11/1991 | Lew ............................ 424/435 |
| 5,084,287 A | 1/1992 | Ghebre-Sellassie et al. . 424/495 |
| 5,100,592 A | 3/1992 | Sparks et al. ................ 264/7 |
| 5,143,662 A | 9/1992 | Chesterfield et al. .......... 264/8 |
| 5,160,743 A | 11/1992 | Edgren et al. ............... 424/473 |
| 5,169,645 A | 12/1992 | Shukla et al. ............... 424/499 |
| 5,183,690 A | 2/1993 | Carr et al. ............... 427/213.31 |
| 5,194,262 A | 3/1993 | Goldberg et al. ............ 424/401 |
| 5,196,199 A | 3/1993 | Fuisz ......................... 424/401 |
| 5,213,810 A | 5/1993 | Steber ......................... 424/490 |
| 5,236,734 A | 8/1993 | Fuisz ......................... 426/641 |
| 5,292,657 A | 3/1994 | Rutherford et al. .......... 435/243 |
| 5,348,758 A | 9/1994 | Fuisz et al. .................. 426/660 |
| 5,380,473 A | 1/1995 | Bogue et al. ................. 264/11 |
| 5,405,617 A | 4/1995 | Gowan, Jr. et al. .......... 424/464 |
| 5,407,676 A | 4/1995 | Fuisz ......................... 424/401 |
| 5,429,836 A | 7/1995 | Fuisz ......................... 426/601 |
| 5,433,951 A | 7/1995 | Serajuddin et al. .......... 424/486 |
| 5,456,932 A | 10/1995 | Fuisz et al. .................. 426/548 |
| 5,461,089 A | 10/1995 | Handyside et al. .......... 523/171 |
| 5,500,162 A | 3/1996 | Theisen et al. ................ 264/9 |
| 5,501,858 A | 3/1996 | Fuisz ......................... 424/439 |
| 5,505,983 A | 4/1996 | Kamada ..................... 427/2.21 |
| 5,518,730 A | 5/1996 | Fuisz ......................... 424/426 |
| 5,539,000 A | 7/1996 | Leonard ..................... 514/682 |
| 5,549,917 A | 8/1996 | Cherukuri et al. ............ 426/96 |
| 5,556,652 A | 9/1996 | Cherukuri et al. ............ 426/5 |
| 5,569,467 A | 10/1996 | Ruiz ........................... 424/489 |
| 5,582,855 A | 12/1996 | Cherukuri et al. ............ 426/5 |
| 5,597,416 A | 1/1997 | Fuisz et al. ................... 127/30 |
| 5,597,844 A | 1/1997 | Chauhan et al. ............. 514/400 |
| 5,601,761 A | 2/1997 | Hoffman et al. ............. 264/4.3 |
| 5,605,889 A | 2/1997 | Curatolo et al. .............. 514/29 |
| 5,633,006 A | 5/1997 | Catania et al. .............. 424/441 |
| 5,683,720 A | 11/1997 | Myers et al. ................ 424/489 |
| 5,690,959 A | 11/1997 | Palepu et al. ................ 424/472 |
| 5,705,190 A | 1/1998 | Broad et al. ................ 424/465 |
| 5,707,646 A | 1/1998 | Yajima et al. ............... 424/439 |
| 5,733,577 A | 3/1998 | Myers et al. ................ 424/488 |
| 5,741,519 A | 4/1998 | Rosenberg et al. .......... 424/464 |
| 5,744,180 A | 4/1998 | Cherukuri et al. ............ 426/99 |

(Continued)

FOREIGN PATENT DOCUMENTS

| EP | 0080341 | 6/1983 |
| EP | 0109253 | 5/1984 |
| EP | 0582396 | 2/1994 |
| EP | 0925789 | 6/1999 |
| EP | 0943341 | 9/1999 |
| EP | 0776658 | 2/2000 |
| EP | 1127580 | 8/2001 |
| GB | 2066070 | 7/1981 |
| GB | 2091097 | 7/1982 |
| IN | 187487 | 5/2000 |

(Continued)

OTHER PUBLICATIONS

Savolainen, Marja et al., International Journal of Pharmaceutics, Aug. 27, 2003, vol. 262, No. 1-2., pp. 47-62, "Evaluation of polar lipid-hydrophilic polymer microparticles.".

Foulds, G., et al., "The effects of an antacid or cimetidine on the serum concentrations of azithromycin", J. Clin. Pharmacol. Feb. 1991; 31(2): 164-7 (Abstract).

(Continued)

Primary Examiner—S. Tran
(74) Attorney, Agent, or Firm—Chernoff, Vilhauer, McClung & Stenzel, LLP

(57) ABSTRACT

A process is described for producing drug-containing multi-particulates with improved stability, characterized by an improvement in one or more of chemical stability, physical stability, or dissolution stability.

19 Claims, No Drawings

U.S. PATENT DOCUMENTS

| | | | |
|---|---|---|---|
| 5,747,058 A | 5/1998 | Tipton et al. | 424/423 |
| 5,766,521 A | 6/1998 | Le Thiesse et al. | 264/7 |
| 5,792,474 A | 8/1998 | Rauchfuss | 424/489 |
| 5,824,342 A | 10/1998 | Cherukuri et al. | 424/484 |
| 5,840,334 A | 11/1998 | Raiden et al. | 424/464 |
| 5,849,223 A | 12/1998 | Myers et al. | 264/15 |
| 5,851,553 A | 12/1998 | Myers et al. | 424/488 |
| 5,851,555 A | 12/1998 | Sanghvi et al. | 424/464 |
| 5,855,915 A | 1/1999 | Pinkus | 242/486 |
| 5,869,098 A | 2/1999 | Misra et al. | 424/484 |
| 5,869,101 A | 2/1999 | Moller et al. | 424/489 |
| 5,883,103 A | 3/1999 | Burnside et al. | 514/262 |
| 5,891,845 A | 4/1999 | Myers | 514/11 |
| 5,912,030 A | 6/1999 | Huzinec et al. | 426/3 |
| 5,919,489 A | 7/1999 | Saleki-Gerhardt et al. | 424/501 |
| 5,935,600 A | 8/1999 | Cherukuri et al. | 424/464 |
| 5,948,407 A | 9/1999 | McGuinness et al. | 424/184.1 |
| 5,952,004 A | 9/1999 | Rudnic et al. | 424/455 |
| 5,958,452 A | 9/1999 | Oshlack et al. | 424/457 |
| 5,965,161 A | 10/1999 | Oshlack et al. | 424/457 |
| 5,965,164 A | 10/1999 | Fuisz et al. | 424/489 |
| 5,972,373 A | 10/1999 | Yajima et al. | 424/439 |
| 5,980,941 A | 11/1999 | Raiden et al. | 424/464 |
| 6,010,718 A | 1/2000 | Al-Razzak et al. | 424/464 |
| 6,013,280 A | 1/2000 | Frisbee et al. | 424/464 |
| 6,048,541 A | 4/2000 | Mirsa et al. | 424/401 |
| 6,051,253 A | 4/2000 | Zettler et al. | 424/465 |
| 6,068,859 A | 5/2000 | Curatolo et al. | 424/490 |
| 6,077,541 A | 6/2000 | Chen et al. | 424/480 |
| 6,083,430 A | 7/2000 | Fuisz et al. | 264/5 |
| 6,086,920 A | 7/2000 | Frisbee et al. | 424/489 |
| 6,090,830 A | 7/2000 | Myers et al. | 514/356 |
| 6,103,264 A | 8/2000 | Hoffmann et al. | 424/468 |
| 6,117,452 A | 9/2000 | Ahlgren et al. | 424/468 |
| 6,139,872 A | 10/2000 | Walsh | 424/464 |
| 6,165,512 A | 12/2000 | Mezaache et al. | 424/489 |
| 6,221,368 B1 | 4/2001 | Breitenbach et al. | 424/400 |
| 6,245,903 B1 | 6/2001 | Karimian et al. | 536/7.4 |
| 6,248,363 B1 | 6/2001 | Patel et al. | 424/497 |
| 6,261,599 B1 | 7/2001 | Oshlack et al. | 424/457 |
| 6,268,489 B1 | 7/2001 | Allen et al. | 536/7.4 |
| 6,270,804 B1 | 8/2001 | Getz et al. | 424/490 |
| 6,316,473 B1 * | 11/2001 | Shimojo et al. | 514/336 |
| 6,328,993 B1 | 12/2001 | Linder et al. | 424/451 |
| 6,335,033 B2 | 1/2002 | Oshlack et al. | 424/457 |
| 6,365,574 B2 | 4/2002 | Singer et al. | 514/29 |
| 6,383,512 B1 | 5/2002 | Linder et al. | 424/436 |
| 6,395,300 B1 | 5/2002 | Straub et al. | 424/489 |
| 6,423,345 B2 | 7/2002 | Bernstein et al. | 424/501 |
| 6,500,459 B1 | 12/2002 | Chhabra et al. | 424/474 |
| 6,551,616 B1 | 4/2003 | Notario et al. | 424/464 |
| 6,569,463 B2 | 5/2003 | Patel et al. | 424/497 |
| 6,576,258 B1 | 6/2003 | Kofler et al. | 424/458 |
| 6,645,528 B1 | 11/2003 | Straub et al. | 424/489 |
| 6,682,759 B2 | 1/2004 | Lim et al. | 424/468 |
| 6,689,390 B2 | 2/2004 | Bernstein et al. | 424/501 |
| 6,692,767 B2 | 2/2004 | Burnside et al. | 424/489 |
| 2001/0003590 A1 | 6/2001 | Joachim et al. | 424/465 |
| 2001/0006650 A1 | 7/2001 | Burnside et al. | 424/400 |
| 2002/0009433 A1 | 1/2002 | Curatolo et al. | 424/94.1 |
| 2002/0025342 A1 | 2/2002 | Linder et al. | 424/489 |
| 2002/0044968 A1 | 4/2002 | Van Lengerich | 424/469 |
| 2003/0004204 A1 * | 1/2003 | Sakalosky | 514/410 |
| 2003/0165563 A1 | 9/2003 | Murphy et al. | 424/465 |
| 2003/0190365 A1 | 10/2003 | Fergione et al. | 424/489 |
| 2003/0228357 A1 | 12/2003 | Johnson et al. | 424/465 |
| 2004/0014951 A1 | 1/2004 | Dumic et al. | 536/7.1 |
| 2004/0023898 A1 | 2/2004 | Dunne | |
| 2004/0121003 A1 | 6/2004 | Chickering, III et al. | 424/465 |
| 2005/0026851 A1 | 2/2005 | Danilovski et al. | 514/28 |

FOREIGN PATENT DOCUMENTS

| | | |
|---|---|---|
| WO | WO 9107171 | 5/1991 |
| WO | WO 9400112 | 1/1994 |
| WO | WO 9427557 | 12/1994 |
| WO | WO 9505805 A1 * | 3/1995 |
| WO | WO 9509601 | 4/1995 |
| WO | WO 9806714 | 2/1998 |
| WO | WO 9818610 | 5/1998 |
| WO | WO 9846239 | 10/1998 |
| WO | WO 9856357 | 12/1998 |
| WO | WO 9903453 | 1/1999 |
| WO | WO 9924031 | 5/1999 |
| WO | WO 0026285 | 5/2000 |
| WO | WO 0057886 | 10/2000 |
| WO | WO 0142221 | 6/2001 |
| WO | WO 0178688 | 10/2001 |
| WO | WO 0185135 | 11/2001 |
| WO | WO 0224174 | 3/2002 |
| WO | WO 02064121 | 8/2002 |
| WO | WO 03018031 | 3/2003 |
| WO | WO 03032922 | 4/2003 |
| WO | WO 03037304 | 5/2003 |
| WO | WO 03053402 | 7/2003 |
| WO | WO 03063832 | 8/2003 |
| WO | WO 03063833 | 8/2003 |
| WO | WO 03063834 | 8/2003 |
| WO | WO 03068191 | 8/2003 |
| WO | WO 03105810 | 12/2003 |
| WO | WO 04000865 | 12/2003 |
| WO | WO 2004009608 | 1/2004 |
| WO | WO 2004035063 | 4/2004 |
| WO | WO 2004087096 | 10/2004 |

OTHER PUBLICATIONS

Amsden, G.W., et al., "Serum and WBC pharmacokinetics of 1500 mg of azithromycin when given either as a single dose or over a 3 day period in healthy volunteers", J. Antimicrobial Chemotherapy (2001), 47(1), 61-66 (Abstract).

Zithromax® azithromycin tablet 250 mg, Quantitative Composition of the Tablet Blend.

Zithromax® azithromycin for oral suspension composition 200 mg/5mL, 200mg/5mL Drug Product.

Zithromax® azithromycin for oral suspension composition 1 gram sachet, Quantitative Composition of the Drug Product.

Zithromax® azithromycin for oral suspension composition 100 mg/5mL, Quantitative Compositions of the Drug Products.

Zithromax® (azithromycin tablets and azithromycin for oral suspension), Full U.S. Prescribing Information, 70-5179-00-4.

Zithromax® (azithromycin capsules) (azithromycin tablets) and (azithromycin for oral suspension), Full U.S. Prescribing Information, 69-4763-00-9.

Food and Drug Administration Center for Drug Evaluation and Research Approved Drug Products with Therapeutic Evaluations, 24th Edition, Orange Book Listings of Azithromycin Dosage Forms.

Barber, J., "Assignments of the $^{13}C$ and $_1H$ NMR Spectra of Azithromycin in $CDCl_3$," Magnetic Resonance in Chemistry 29:7(1991)740-743.

Barthelemy, P., et al., "Compritol® 888 ATO: An Innovative Hot-Melt Coating Agent for Prolonged-Release Drug Formulations," Europ. J. Pharmaceut. and Biopharmaceutics, 47(1999)87-90.

Bhagwatwar, H., et al., "Preparation of Drug-Containing Wax Microspheres Using a Melt Dispersion Technique," Pharmaceutical Research, 6:7(1989)S-177, Abstract No. PD 1201.

Breitenbach, J., et al., "Solid Dispersions by an Integrated Melt Extrusion System," Proceed. Int'l Symp. Control. Re. Bioact. Materials, 25(1998)804-805.

Craig, D.Q.M., "The Physical Characterisation of Gelucire 50/13," Bulletin Technique Gattefosse, 89(1996)39-51.

DeMan, J.M., et al., "Thermal Analysis Microscopy for the Study of Phase Changes in Fats," Food Microstructure, 4(1985)233-239.

Eldem T., et al., "Polymorphic Behavior of Sprayed Lipid Micropellets and Its Evaluation by Differential Scanning Calorimetry and Scanning Electron Microscopy," *Pharmaceutical Research*, 8:2(1991)178-184.

Eldem, T., et al., "Optimization of Spray-Dried and -Congealed Lipid Micropellets and Characterization of Their Surface Morphology by Scanning Electron Microscopy," Pharmaceutical Research, 8:1(1991)47-54.

Emas, M., and H. Nyqvist, "Methods of Studying Aging and Stabilization of Spray-Congealed Solid Dispersions with Carnauba Wax. 1. Microcalorimetric Investigation," *Int'l J. Pharmaceutics*, 197(2000)117-127.

Faham, A., et al., "Hot-Melt Coating Technology. I. Influence of Compritol 888 Ato and Granule Size on Theophylline Release," *Drug Dev. Industrial Pharm.*, 26:2(2000)167-176.

Follonier, N., et al, "Hot-Melt Extruded Pellets for the Sustained Release of Highly Dosed Freely Soluble Drugs," *Proceed. Intern. Symp. Control. Release Bioactive Materials*, 18(1991)578-579.

Forster, A., et al., "Characterization of Glass Solutions of Poorly Water-Soluble Drugs Produced by Melt Extrusion with Hydrophilic Amorphous Polymers," *J. Pharmacy Pharmacology*, 53(2001)303-315.

Foulds, G., et al., "The Absence of an Effect of Food on the Bioavailability of Azithromycin Administered as Tablets, Sachet or Suspension," *J. Antimicrobial Chemotherapy*, 37:Suppl. C(1996)37-44.

Gattefosse, "Gelucire® —Pharmaceutical Excipients for Oral Semi-Solid Formulations," Technical Dossier, $2^{nd}$ edition, Gattefosse s.a., Cedex, France (1996).

Ghali, E.S., et al., "Thermal Treatment of Beads with Wax for Controlled Release," *Drug Development and Industrial Pharmacy*, 15:9(1989)1311-1328.

Hancock, B.C., and G. Zografi, "The Relationship Between the Glass Transition Temperature and the Water Content of Amorphous Pharmaceutical Solids," *Pharmaceutical Research*, 11:4(1994)471-477.

Joachim, J., et al., "Le Compritol*, Etudes Galenique, Physique et Statstique," *APGI*, IV(1989)291-296.

Johnson, D.E., et al., "A New Method for Coating Glass Beads for Use in Gas Chromatography of Chloropromazine and Its Metabolites," Source unknown, and date unknown. (May be 1964-1965).

Jorgensen, K., et al., "Dissolution Stability of Multiparticulate Controlled Release Tablets," *Int'l J. Pharmaceutics*, 153(1997)1-11.

Meshall, M.M., et al., "Optimization of Theophylline Release from Tablets Containing Compritol," *S.T.P. Pharma Sciences*, 5:6(1995)429-434.

Perez, M. deLos A, et al., "Sustained Release Phenylpropanolamine Hydrochloride from Compritol ATO-888 Matrix," *Pharmaceutical Research*, 9:10(1992)S-162, Abstract No. PT6191.

Perez, M.A., et al., "Sustained Release Phenylpropanolamine Hydrochloride from ATO 888 Matrix," *PRHSJ*, 12:4(1993)263-267.

Perissutti, B., et al., "Solid Dispersions of Carbamazepine with Gelucire 44/14 and 50/13," *S.T.P. Pharma Sciences*, 10:6(2000)479-484.

Physician's Desk Reference, Information cited on ZITHROMAX® capsules (equivalent to 250 mg azithromycin), tablets (equivalent to 600 mg azithromycin), and oral suspension (equivalent to 1 g azithromycin).

Reilly, W.J. Jr., and J.B. Schwartz, "A Potential Controlled Release Wax Matrix Excipient," *Pharmaceutical Research*, 8:10(1991)98, supplement, Abstract No. PT6108.

Reis, R. and F. Moll, "Matrix Formation of Polyglycolic Acid Tablets by Annealing," *European J. Pharm. and Biopharm.*, 40:1(1994)14-18.

Rxlist.com, "Azithromycin," description of drug, categories, brand names, from internet website, Mar. 14, 2001.

San Vincente, A., et al., "Effect of Aging on the Release of Salbutamol Sulfate from Lipid Matrices," *Int'l J. Pharmaceutics*, 208(2000)13-21).

Schwartz, J.B., et al., "A Potential Controlled Release Wax Matrix Excipient for Tablets," *Pharmaceutical Research*, 9:10(1992)S-162, Abstract No. PT6189.

Schwartz, J.B., et al., Preliminary Evaluation of Controlled Release Agents for Tablets, *Pharmaceutical Research*, 9:10(1992)S-162, Abstract No. PT6190.

Sugao, H., et al, "Taste Masking of Bitter Drug Powder without Loss of Bioavailability by Heat Treatment of Wax-Coated Microparticles," *J. Pharmaceutical Sci.*, 87:1(1998)96-100.

Thomsen, L.J., et al., "Prolonged Release Matrix Pellets Prepared by Melt Pelletization. I. Process Variables," *Drug Development and Industrial Pharmacy*, 19:15(1993)187-1887.

Wang, A.E. and J.B. Schwartz, "Effect of Temperature on Drug Release from Wax Matrix Tablets After Thermal Treatment," *Pharmaceutical Research*, 11:10(1994)S-155, Abstract No. 6099.

Zhang, Y.-E., et al., Effect of Processing Methods and Heat Treatment on the Formation of Wax Matrix Tablets for Sustained Drug Release, *Pharm. Dev. Technol.*, 6:2(2001)131-144.

Arguendas, A., "Single Dose Therapy in Otitis Media, *Clinical Microbiology and Infection*," Abstract, S130, vol. 5, Supplemental 3, (1999).

Block, S., et al., "Single-Dose Azithromycin (30 mg/kg) in Acute Otitis Media," ICAAC, New Orleans, LA, Sep. 7-10, 2003, Abstract 174.

Curatolo, W., et al., "Site-Specific Absorption and Toleration of Azithromycin," Proceedings Intern. Symposium Rel. Bioact. Mater., 23, 1996.

Luke, D.R., et al, "Clinical Pharmacology of Azithromycin Given at Various Sites Along the Gastrointestinal Tract in Healthy Subjects," pp. 464-468.

Physicians Desk Reference, "*Appendix A Summary of Pediatric Suspension Commercial Products*," $55^{th}$ edition, Phase III Clinical Dosage Form Nomination, pp. 19 and 28 (2001).

Pfizer, Inc., Zithromax [package insert], "*Zithromax (azithromycin tablets) and (azithromycin for oral suspension)*," www.pfizer.com/download/uspi_zithromax.pdf (2004).

* cited by examiner

MULTIPARTICULATE COMPOSITIONS WITH IMPROVED STABILITY

The present application claims the priority benefit of U.S. Provisional Application No. 60/527,245, filed on Dec. 4, 2003. The contents of the priority document are herein incorporated by reference.

BACKGROUND OF THE INVENTION

Multiparticulates are well-known dosage forms that comprise a multiplicity of particles whose totality represents the intended therapeutically useful dose of a drug. When taken orally, multiparticulates generally disperse freely in the gastrointestinal tract, maximize absorption, and minimize side effects. See, for example, *Multiparticulate Oral Drug Delivery* (Marcel Dekker, 1994), and *Pharmaceutical Pelletization Technology* (Marcel Dekker, 1989).

It is well known that some drugs are capable of existing in several different crystalline forms. A specific example of a drug that may exist in one of several crystalline forms is azithromycin, for which many different crystalline forms have been identified thus far. See commonly owned U.S. patent application Publication No. 20030162730. The most stable form of azithromycin at ambient temperature and humidity (e.g., 25° C. and 50% relative humidity) is the crystalline dihydrate, described in U.S. Pat. No. 6,268,489, which is a crystalline form that includes water.

It is known that some drug multiparticulate formulations, especially those using a lipid or glyceride-based carrier, show changes in performance upon aging under controlled conditions. See, for example, San Vicente et al., 208 *Intl. J. Pharm.* 13 (2000), U.S. Pat. No. 5,213,810, Jorgensen et al., 153 *Intl. J. Pharm.* 1 (1997), Eldem et al., 8 *Pharm. Res.* 47 (1991) and Eldem et al., 8 *Pharm. Res.* 178 (1991). The observed changes in performance are often attributed to changes in the morphology of the carrier over time, but there is no disclosure or suggestion of any method to prevent such changes in morphology.

Product literature provided by Gattefossé, makers of Gelucire® products (mixtures of fatty acid esters of glycerol and polyethylene glycol) suggest heat treatment of Gelucir®-based drug formulations filled into hard gelatin capsules. *Gelucire® Technical Dossier* (2d Ed 1996). However, the use of such a process for stabilization of multiparticulates is not disclosed.

Bulletin Technique Gattefossé No. 89, page 47, (1996) discloses that drug release from formulations containing Gelucire® bases may change with storage, but concedes that very little is known regarding how to prevent such changes.

U.S. Pat. Nos. 5,597,416, 5,869,098, 6,048,541, and 6,165,512 all disclose a process for crystallizing sugars in an amorphous feedstock by exposing the feedstock to a crystallization enhancer, such as ethanol. However, there is no suggestion of using such a process to stabilize a drug-containing multiparticulate.

Thus, there is a need in the art for processes for forming drug-containing multiparticulates that have improved stability. This invention addresses that need.

BRIEF SUMMARY OF THE INVENTION

The inventors have discovered that the drawbacks outlined above can be overcome by treating such multiparticulates with controlled heat and/or with a mobility-enhancing agent following their formation, resulting in an increase in drug crystallinity, and in some embodiments, an improved chemical stability, physical stability, and/or dissolution stability.

In a first aspect, the invention provides a process for producing multiparticulates comprising the steps of (a) forming multiparticulates comprising a drug and a pharmaceutically acceptable carrier, the carrier having a melting point of $T_m°$ C.; and (b) post-treating the multiparticulates by at least one of (i) heating them to a temperature of at least about 35° C. and less than about ($T_m°$ C.-10° C.), or (ii) exposing them to a mobility-enhancing agent, wherein the post-treatment is conducted for a period of time sufficient to achieve a drug crystallinity in the multiparticulates that is greater than the crystallinity of the drug in a control composition of the multiparticulates of step (a).

In a second aspect, the invention provides pharmaceutical compositions comprising drug-containing multiparticulates made by the inventive process.

In a third aspect, the invention also provides for a method of treating a patient in need of drug treatment by administering to the patient a therapeutically effective amount of a pharmaceutical composition of the invention.

DETAILED DESCRIPTION OF THE INVENTION

A primary object of the present invention is to provide drug multiparticulate compositions with high drug crystallinity and optimally, with improved stability, characterized by any or all of improved chemical stability, improved physical stability, or improved dissolution stability.

The term "multiparticulate" is intended to embrace a dosage form comprising a multiplicity of particles whose totality represents the intended therapeutically useful dose of the drug. The particles generally have a mean diameter of from about 40 to about 3000 µm, preferably from about 50 to 1000 µm, and most preferably from about 100 to about 300 µm. While a multiparticulate can have any shape and texture, normally, it is spherical with a smooth surface.

As used in the present invention, the term "about" means the specified value ±10% of the specified value.

The term "carrier" is defined as a pharmaceutically acceptable material primarily used as either a matrix or to control the rate of release of drug, or both. The carrier may be a single material or a mixture of two or more materials.

The phrase "aqueous environment of use" as used herein, refers either to in vivo fluids or to an in vitro test medium. "Introduction" to a use environment includes either ingestion where the use environment is in vivo, or being placed in a test medium where the use environment is in vitro.

The term "patient" embraces all animals, particularly mammals, and especially humans, though any animal that can benefit from the use of a drug is considered to be within the scope of the invention.

Post-Treatment of Multiparticulates

As mentioned in the Background, some multiparticulate dosage forms show changes in performance upon aging. Without wishing to be bound by any particular theory or mechanism of action, it is believed that when multiparticulates are made by various processes, they are initially in a thermodynamically unstable form, meaning that the drug and carrier used in the composition are initially not in their lowest energy state. As a result, the physical state of the materials changes as they return to a lower energy state over time. This return to a lower energy state is often characterized by changes in the physical nature, chemical stability, or dissolution performance of the multiparticulate.

For example, the solubility of a drug in a carrier is a function of the temperature, physical state (e.g., amorphous or crystalline and, if crystalline, the crystalline form), and moisture or solvent content of the carrier. Often, solubility increases with increasing temperature. In some multiparticulate-formation processes, the drug and carrier are exposed to temperatures that are greater than typical storage temperatures (e.g., up to 40° C.) for the multiparticulates. As a result, the solubility of drug in the carrier during the multiparticulate manufacturing process is greater than its solubility at storage conditions. During the multiparticulate formation process, a portion of the crystalline drug will dissolve into the molten carrier up to the drug's solubility limit in the molten carrier at the processing conditions. When the molten carrier is initially cooled to form the multiparticulates, the multiparticulate will consist of particles of crystalline drug substance encapsulated in a solid solution of carrier and the dissolved drug. Upon further cooling, the solubility of the drug in the carrier will decrease, resulting in crystalline drug encapsulated in a supersaturated solid solution of non-crystalline drug in the carrier. Over time, the concentration of non-crystalline drug in this supersaturated solid solution will decrease until the drug reaches its solubility limit in the carrier. The non-crystalline drug above this solubility limit will form drug-rich regions in the multiparticulate (that is, it will phase separate from the solid solution). The multiparticulate thus consists of crystalline drug encapsulated in carrier, and non-crystalline drug in drug-rich regions. The drug in these drug-rich regions may remain in a non-crystalline (that is, amorphous) state or, in some cases, it may crystallize over time, leading to further changes in the physical state of all or a portion of the drug over time. This change in the state of the drug in the carrier can also lead to changes in the dissolution rate of the drug from the multiparticulates. In addition, drug in a non-crystalline state is often more susceptible to chemical degradation than crystalline drug; as a result, the drug in the multiparticulate may have decreased chemical stability.

Other multiparticulate manufacturing processes use liquids or solvents in which the drug is highly soluble. In such processes, a portion of the drug is dissolved in the liquid during the multiparticulate manufacturing process. When the liquid is subsequently removed from the multiparticulate, the drug may precipitate, for example, as an amorphous solid. As indicated above, this can lead to physical instability, chemical instability, or dissolution instability of the drug in the multiparticulate.

Additionally, it is also well known that some carriers, especially fats such as glyceryl esters, when rapidly congealed from a molten state, can be at least partially present in an amorphous state or in a crystalline state other than their most stable crystalline state, such high-energy crystalline states being termed unstable polymorphs. Over time, the physical state of the fat may change, generally converting to the stable polymorph. Such changes in the physical state of the carrier can lead to instability of the drug in the multiparticulate over time. Specifically, the drug is generally less soluble in crystalline fat relative to amorphous fat and thus, as the fat crystallizes, any dissolved drug may separate into a drug-rich crystalline or amorphous phase.

Likewise, when the multiparticulates comprises a carrier and one or more optional excipients, the solubility of the optional excipient in the carrier during the multiparticulate manufacturing process can be greater than its solubility at typical storage conditions. As noted above for the case of the solubility of drug in the carrier, over time, the optional excipient can separate into excipient-rich regions that are rich in the excipient, and carrier-rich regions that are rich in the carrier. Such changes in the physical state of the multiparticulate components can lead to instability of the multiparticulate.

Other changes in the multiparticulates can occur over time, in part due to the relaxation of the drug or carrier to a lower energy state, including changes in porosity, the interconnectivity of pores, and the size and number of voids in the multiparticulate. These changes can also lead to changes in the dissolution performance of the multiparticulate over time.

In each of these instances, changes in the physical state of the drug or carrier present in the multiparticulates can lead to physical, chemical or dissolution instability in the multiparticulates. The inventors have discovered that the stability of multiparticulates can be improved by use of the post-treatment process described herein.

Generally, the post-treatment conditions are selected so that the drug and the carrier substantially revert to their lower energy states. This is accomplished through exposure of the multiparticulate to elevated temperatures, exposure to a mobility-enhancing agent, or to both. As described above, the lower energy state of the drug will normally be a crystalline state. Thus, preferably, post-treatment conditions are chosen such that any amorphous drug or drug dissolved in the carrier that was formed is substantially converted back to a crystalline state. Preferably, the crystalline state is the same crystalline state that the drug was in prior to formation of the multiparticulate.

In one aspect, the multiparticulates are post-treated by exposure to elevated temperatures. The inventors have discovered that the higher the post-treatment temperature, the faster the drug and/or carrier will revert to their lower energy states. Thus, the post-treatment process is preferably performed at a temperature of at least about 35° C., more preferably at least about 40° C.

However, it the post-treatment temperature is too high, damage may occur to the multiparticulates, or they may agglomerate during the post-treatment process, altering their dissolution performance. Thus, the post-treatment process should be performed at a temperature of less than about $(T_m-10°$ C.), where $T_m$ is the melting point of the carrier in ° C. As used herein "melting point of the carrier" means the temperature at which the carrier, when containing the drug and any optional excipients present in the multiparticulate, transitions from its crystalline to its liquid state. When the carrier is not crystalline, "melting point of the carrier" means the temperature at which the carrier becomes fluid in the sense that it will flow when subjected to one or more forces such as pressure, shear, and centrifugal force, in a manner similar to a crystalline material in the liquid state. The inventors have found that when the post-treatment process is performed below this temperature, the multiparticulates are not damaged and agglomeration is minimized.

Such a post-treatment can be conducted in any apparatus that controls the temperature of the multiparticulates. Examples of such equipment are well known in the art, and include tray dryers, ovens, fluidized beds, twin-shell mixers, extruders such as single-screw and twin-screw extruders, and V-blenders. The multiparticulates may be placed in such apparatus while exposed to the ambient atmosphere, or they may be exposed to a controlled atmosphere, such as an atmosphere containing a mobility-enhancing agent, as described below. Alternatively, the multiparticulates may be sealed in a container, such as a bottle, box, barrel, pouch, or bag, and the container then placed into the temperature controlled apparatus.

In a separate aspect, the multiparticulates may also be post-treated simply by exposure to a mobility-enhancing agent. The mobility-enhancing agent increases the mobility of the drug in the multiparticulate, allowing the drug and/or carrier to more rapidly form into lower energy states. By "mobility" is meant the movement or diffusion of drug and/or carrier in the multiparticulate. The mobility-enhancing agent accomplishes this by being at least partially absorbed into the multiparticulate. Suitable mobility-enhancing agents include water, methanol, ethanol, propanol and its isomers, butanol and its isomers, acetone, methyl ethyl ketone, methyl isobutyl ketone, ethyl acetate, tetrahydrofuran, acetonitrile, cyclohexane, formic acid, acetic acid, and mixtures thereof. The mobility-enhancing agent may be present as a liquid, a vapor, or a mixture of a liquid and vapor during the post-treatment process. For example, the post-treatment process can be conducted by spraying the mobility-enhancing agent in liquid form onto the multiparticulates in a suitable vessel, such as a twin-shell blender. Alternatively, the multiparticulates may be contacted with a gas stream containing the mobility-enhancing agent, such as in a fluidized bed apparatus. In any case, the mobility-enhancing agent should be added to the multiparticulates in such a manner that the concentration of mobility-enhancing agent is substantially uniform throughout the multiparticulates being treated.

The amount of mobility-enhancing agent needed to post-treat the multiparticulates will depend on the mobility-enhancing agent used and the characteristics of the drug, the carrier, and other optional excipients in the multiparticulate. Upon exposure, the mobility-enhancing agent is absorbed by the multiparticulates. Thus, a sufficient quantity of mobility-enhancing agent should be used to increase the mobility of the drug and/or carrier so that they can rapidly substantially revert to their lower energy states. When the mobility-enhancing agent is added in the vapor phase, the amount of gas containing the mobility-enhancing agent must be sufficiently large that a sufficient amount of agent is absorbed by the multiparticulates. In addition, the agent-containing gas must contact the multiparticulates in a manner and for a sufficient duration for the vapor to be adequately absorbed by the multiparticulates.

One method to determine the amount of mobility-enhancing agent needed to post-treat the multiparticulates is as follows. A sample of the multiparticulates and a quantity of the mobility-enhancing agent are sealed into a container, such as a flask or vial. The quantity of mobility-enhancing agent is such that if all of the mobility-enhancing agent evaporated into the volume of the container it would be about 50% of the saturation vapor pressure of the mobility-enhancing agent at the conditions of the test. Samples of the multiparticulates are then periodically removed from the container and analyzed for crystallinity of the drug by PXRD or some other quantitative method. This test is then repeated with other quantities of mobility-enhancing agent being placed into the container, such as about 75% of the saturation vapor pressure and about 95% of the saturation vapor pressure. A quantity of mobility-enhancing agent greater than 100% of the saturation vapor pressure may also be used. From these data, the relationship between the amount of mobility-enhancing agent needed to post-treat the multiparticulates and the time to post-treat the multiparticulates can be determined.

Once the post-treatment process has been completed, a portion of the mobility-enhancing agent is often removed from the multiparticulate. In some cases, a portion of the mobility-enhancing agent is removed from the multiparticulate during the post-treatment process, such as by evaporation, tray drying, vacuum drying, and other methods known in the art. See for example, *Remington: The Science and Practice of Pharmacy*, 20th Edition (2000).

An especially preferred form of post-treatment is to expose the multiparticulates to the mobility-enhancing agent in a vaporized state. For example, when the mobility-enhancing agent is water, the multiparticulates may be exposed to a gas-phase atmosphere, such as nitrogen or air, having a relative humidity (RH) of greater than about 10%, more preferably greater than about 30%, and most preferably greater than about 50%.

In another aspect, the post-treatment process may also be conducted by exposure of the multiparticulates to a mobility-enhancing agent at elevated temperatures. In such cases, the multiparticulates may first be exposed to the mobility-enhancing agent as described above, and then exposed to elevated temperatures using the equipment and processes previously described. Alternatively, the multiparticulates may be exposed to the mobility-enhancing agent at an elevated temperature. For example, the multiparticulates may be placed in a suitable container, such as a fluidized bed equipped with a heated fluidizing gas, and the mobility-enhancing agent sprayed onto the multiparticulates. Alternatively, a heated gas containing the mobility-enhancing agent may be introduced into the fluidized bed containing the multiparticulates.

When conducting such post-treatment processes, it is preferred that the mobility-enhancing agent is absorbed by the multiparticulates at the processing temperature. In addition, it is preferred that the post-treatment process be conducted at a temperature of at least about 35° C., preferably at least about 40° C., and less than about ($T_m$-10° C.). One skilled in the art will realize that the value of $T_m$ may be affected by the amount of mobility-enhancing agent present in the multiparticulates and the post-treatment temperature should therefore be chosen accordingly.

The post-treatment time should be sufficiently long to allow an increase in the crystallinity of the drug in the multiparticulates and/or to reach a sufficiently stable, low-energy state, while at the same time not so long so as to be impractical from a commercial manufacturing standpoint. Generally, it is preferred that the post-treatment time be about 8 weeks or less, preferably about 6 weeks or less, and most preferably about 4 weeks or less. The post-treatment time required to achieve a stable composition will vary with the post-treatment temperature, with shorter times being required at higher temperatures and longer times being required at lower temperatures.

One especially effective post-treatment comprises exposing the multiparticulates to a temperature between about 40° C. and about 50° C., and to an atmosphere of air with a vapor-phase water content between about 50% RH and 100% RH for a time of about 1 to about 30 days, preferably about 5 to about 20 days, and most preferably about 10 days. Such a post-treatment can be conducted in any apparatus that allows the multiparticulates to be contacted with the humid air such that there is a controlled temperature and humidity. Examples of such equipment include tray dryers, environmental ovens, fluidized beds, twin-shell mixers, twin-screw extruders and V-blenders. Due to variations in the uniformity of temperature and humidity in such equipment, one must ensure that the post-treatment conditions selected will lead to stable multiparticulates in the equipment selected. For example, tests should be performed to ensure that the height of the bed depth in a tray dryer used to post-treat multiparticulates is not so high that the multiparticulates at the bottom of the bed do not absorb the required level of mobility-enhancing agent, such as water, in a sufficiently rapid time such that they are not adequately post-treated to stabilize the drug release rate from the multiparticulates.

In another aspect, the multiparticulates may be post-treated by mixing the mobility-enhancing agent with the multiparticulates and then sealing the mobility-enhancing agent and multiparticulates in a container so as to ensure retention of the mobility-enhancing agent in the multiparticulates, optionally followed by heating the container to the desired post-treatment temperature. Examples of suitable containers include bags, drums, bottles, pouches and boxes. The sealed container containing the multiparticulates and mobility-enhancing agent may then be placed into a heated room or oven held at the desired post-treatment temperature.

In yet another aspect, the mobility-enhancing agent may be incorporated into the multiparticulates during the multiparticulate formation process, so that the mobility-enhancing agent is present in the multiparticulates after formation. To optionally effect post-treatment by heating, the multiparticulates containing the mobility-enhancing agent may be sealed into a container and then the container placed into a temperature-controlled environment, as described above. Specific processes for incorporating a mobility-enhancing agent into the multiparticulates during the formation process are discussed in greater detail below.

The post-treatment process is conducted for a sufficient time that the crystallinity of drug in the multiparticulate is increased relative to a control multiparticulate consisting essentially of the untreated multiparticulate. By "untreated multiparticulate" is meant a multiparticulate that has not been treated by heating and/or by exposure to a mobility-enhancing agent or that has been stored for an extended period of time after formation of the multiparticulate. One skilled in the art will recognize that some storage time between formation of the multiparticulate and evaluation of the multiparticulate is unavoidable; however, this time should be minimized when selecting a control multiparticulate.

By "crystallinity" is meant the fraction of drug in a crystalline state as opposed to a non-crystalline or amorphous state. Generally, the crystallinity of the drug in the multiparticulates increases over time during the post-treatment process. The post-treatment process of the present invention results in an increase in the crystallinity of the drug in the multiparticulate relative to the control multiparticulate described above. At a minimum, the post-treatment process results in an increase in the crystallinity of the drug that is within the accuracy of the method used to determine the crystallinity of the drug in the composition. For example, if the crystallinity of the drug in a multiparticulate is measured as 90±4 wt %, then the multiparticulate post-treated by the process of the present invention will have a crystallinity of greater than 94 wt % when measured using the same instrument or methodology.

The crystallinity of drug in a multiparticulate may be determined using Powder X-Ray Diffraction (PXRD) analysis. In an exemplary procedure, PXRD analysis may be performed on a Bruker AXS D8 Advance Diffractometer. In this procedure, multiparticulate samples weighing about 500 mg are packed in Lucite sample cups and the sample surface smoothed using a glass microscope slide to provide a consistently smooth sample surface that is level with the top of the sample cup. Samples are spun in the φ plane at a rate of 30 rpm to minimize crystal orientation effects. The X-ray source (S/B $KCu_\alpha$, λ=1.54 Å) is operated at a voltage of 45 kV and a current of 40 mA. Data for each sample are collected over a period of about 20 to 60 minutes in continuous detector scan mode at a scan speed of about 1 to 15 seconds/step and a step size of 0.02°/step. Diffractograms are collected over the 2θ range of 4° to 30°.

The crystallinity of the test sample is determined by comparison with two or more calibration standards consisting of physical mixtures of crystalline drug and carrier. Each physical mixture is blended together 15 minutes on a Turbula mixer. Using the instrument software, the area under the diffractogram curve is integrated over the 2θ range using a linear baseline. This integration range includes as many drug-specific peaks as possible while excluding excipient-related peaks. A linear calibration curve of percent crystalline drug versus the area under the diffractogram curve is generated from the calibration standards. The crystallinity of the test sample is then determined using these calibration results and the area under the curve for the test sample. Results are reported as a mean percent drug crystallinity by crystal mass.

In one aspect, the multiparticulates are post-treated for a time sufficient to achieve a degree of drug crystallinity of at least 95%. Preferably, at least 95% of the drug in the post-treated multiparticulate is in the same crystalline state as the drug was prior to formation of the multiparticulates.

A useful way to quantify an increase in drug crystallinity in a multiparticulate is to determine the relative degree of improvement in drug crystallinity in the multiparticulate, meaning the ratio of (1) the amount of non-crystalline drug in a control multiparticulate to (2) the amount of non-crystalline drug in a post-treated multiparticulate. (The amount of non-crystalline drug may be taken as 100 wt % minus the amount of crystalline drug in the multiparticulate.) For example, if the amount of crystalline drug in the control multiparticulate is 80 wt %, and the amount of crystalline drug in the post-treated multiparticulate is 90 wt %, the relative degree of improvement in crystallinity is (100 wt %-80 wt %)/(100 wt %-90 wt %)=20 wt %/10 wt %=2.0.

In one embodiment, the post-treatment process is conducted for a sufficient time that the multiparticulate has a relative degree of improvement in crystallinity of at least 1.1, preferably at least 1.25, more preferably at least 1.5 and even more preferably at least 2.0.

Processes for Forming Multiparticulates

The multiparticulates may be made by any process that results in formation of drug-containing multiparticulates. As mentioned above, the particles generally have a mean diameter of from about 40 to about 3000 μm, although more typically the diameter ranges from about 50 to about 1000 μm. While a multiparticulate can have any shape and texture, normally, it is spherical with a smooth surface.

Preferred processes to form the multiparticulates include thermal-based processes such as melt- and spray-congealing, liquid-based processes, such as extrusion spheronization, wet granulation, spray-coating, spray-drying and other granulation processes such as dry granulation and melt granulation.

In one aspect, the multiparticulates are made by a melt-congeal process comprising the steps of (a) forming a molten mixture comprising a drug and a pharmaceutically acceptable carrier, (b) delivering the molten mixture of step (a) to an atomizing means to form droplets from the molten mixture, and (c) congealing the droplets from step (b) to form multiparticulates. The melt-congeal process is disclosed more fully in commonly assigned U.S. patent application Ser. Nos. 60/527,244 ("Improved Azithromycin Multiparticulate Dosage Forms by Melt-Congeal Processes," and 60/527,315 ("Extrusion Process for Forming Chemically Stable Drug Multiparticulates," filed concurrently herewith.

The molten mixture may comprise (1) drug dissolved in the molten carrier, (2) drug suspended in the molten carrier, (3) carrier suspended in the molten drug, (4) molten drug suspended in the molten carrier, or (5) any combination of such states or those states that lie between. In one preferred embodiment, the molten mixture comprises substantially crystalline drug particles substantially uniformly suspended in a carrier that is substantially fluid. In such cases, a portion of the drug may be dissolved in the fluid carrier and a portion of the carrier may remain solid. Preferably, less than about 30 wt % of the total drug melts or dissolves in the molten carrier.

Thus, by "molten mixture" is meant that the mixture of drug and carrier are heated sufficiently that the mixture becomes sufficiently fluid that the mixture may be formed into droplets or atomized. Atomization of the molten mixture may be carried out using any of the atomization methods described below. Generally, the mixture is molten in the sense that it will flow when subjected to one or more forces such as pressure, shear, and centrifugal force, such as that exerted by a centrifugal or spinning-disk atomizer. Thus, the drug/carrier mixture may be considered "molten" when the mixture becomes sufficiently fluid that it may be atomized. Generally, a mixture is sufficiently fluid for atomization when the viscosity of the molten mixture is less than about 20,000 cp, preferably less than about 15,000 cp, more preferably less than about 10,000 cp. Often, the mixture becomes molten when the mixture is heated above the melting point of one or more of the carrier components, in cases where the carrier is sufficiently crystalline to have a relatively sharp melting point; or, when the carrier components are amorphous, above the softening point of one or more of the carrier components. Thus, the molten mixture is often a suspension of solid particles in a fluid matrix. In one preferred embodiment, the molten mixture comprises a mixture of substantially crystalline drug particles suspended in a carrier that is substantially fluid. In such cases, a portion of the drug may be dissolved in the fluid carrier and a portion of the carrier may remain solid.

Although the term "melt" refers specifically to the transition of a crystalline material from its crystalline to its liquid state, which occurs at its melting point, and the term "molten" refers to such a crystalline material in its liquid state, as used herein, the terms are used more broadly. In the case of "melt," the term refers to the heating of any material or mixture of materials sufficiently that it becomes fluid in the sense that it may be pumped or atomized in a manner similar to a crystalline material in the liquid state. Similarly, "molten" refers to any material or mixture of materials that is in such a fluid state.

Virtually any process can be used to form the molten mixture. One method involves melting the carrier in a tank, adding the drug to the molten carrier, and then mixing the mixture to ensure the drug is uniformly distributed therein. Alternatively, both the drug and carrier may be added to the tank and the mixture heated and mixed to form the molten mixture. When the carrier comprises more than one material, the molten mixture may be prepared using two tanks, meeting a first carrier in one tank and a second in another. The drug is added to one of these tanks and mixed as described above. In another method, a continuously stirred tank system may be used, wherein the drug and carrier are continuously added to a heated tank equipped with means for continuous mixing, while the molten mixture is continuously removed from the tank.

An especially preferred method of forming the molten mixture is by an extruder. By "extruder" is meant a device or collection of devices that creates a molten extrudate by heat and/or shear forces and/or produces a uniformly mixed extrudate from a solid and/or liquid (e.g., molten) feed. Such devices include, but are not limited to single-screw extruders; twin-screw extruders, including co-rotating, counter-rotating, intermeshing, and non-intermeshing extruders; multiple screw extruders; ram extruders, consisting of a heated cylinder and a piston for extruding the molten feed; gear-pump extruders, consisting of a heated gear pump, generally counter-rotating, that simultaneously heats and pumps the molten feed; and conveyer extruders. Conveyer extruders comprise a conveyer means for transporting solid and/or powdered feeds, such, such as a screw conveyer or pneumatic conveyer, and a pump. At least a portion of the conveyer means is heated to a sufficiently high temperature to produce the molten mixture. The molten mixture may optionally be directed to an accumulation tank, before being directed to a pump, which directs the molten mixture to an atomizer. Optionally, an in-line mixer may be used before or after the pump to ensure the molten mixture is substantially homogeneous. In each of these extruders the molten mixture is mixed to form a uniformly mixed extrudate. Such mixing may be accomplished by various mechanical and processing means, including mixing elements, kneading elements, and shear mixing by backflow. Thus, in such devices, the composition is fed to the extruder, which produces a molten mixture that can be directed to the atomizer.

When preparing the molten mixture in which the composition contains crystalline drug and the crystalline form of the drug comprises a volatile species having a vapor pressure of at least 0.01 atm at the maximum temperature of the molten mixture, the drug can be substantially maintained in this form by ensuring that the activity of the volatile species in the molten mixture is sufficiently high that volatile species is not substantially removed from the drug during formation of the multiparticulates. Despite such precautions, a portion of such crystalline drug may dissolve in the molten carrier and, upon dissolution, the volatile species will be partially removed from the drug. However, such precautions will increase the fraction of drug maintained in the drug with volatile species crystalline state. To keep the activity of volatile species in the molten mixture high, it is desirable to keep the gas phase atmosphere above the molten mixture at a high activity of the volatile species. This is disclosed more fully in commonly assigned U.S. patent application Ser. No. 60/527,316 ("Method for Making Pharmaceutical Multiparticulates," filed concurrently herewith.

Once the molten mixture has been formed, it is delivered to an atomizer that breaks the molten feed into small droplets. Virtually any method can be used to deliver the molten mixture to the atomizer, including the use of pumps and various types of pneumatic devices such as pressurized vessels or piston pots. When an extruder is used to form the molten mixture, the extruder itself can be used to deliver the molten mixture to the atomizer. Typically, the molten mixture is maintained at an elevated temperature while delivering the mixture to the atomizer to prevent solidification of the mixture and to keep the molten mixture flowing.

The feed is preferably molten prior to congealing for at least 5 seconds, more preferably at least 10 seconds, and most preferably at least 15 seconds so as to ensure adequate homogeneity of the drug/carrier melt. The molten mixture preferably also remains molten for no more than about 20 minutes to limit degradation of the drug. For some drug/carrier combinations, it may be desirable to further reduce the time that drug is in the molten mixture to well below 20 minutes in order to further limit drug degradation to an acceptable level. In such cases, such mixtures may be maintained in the molten state for less than 15 minutes, and in some cases, even less than 10 minutes. When an extruder is used to produce the molten feed, the times above refer to the mean time from when material is introduced to the extruder to when the molten mixture is congealed. Such mean times can be determined by procedures well known in the art. In one exemplary method, a small amount of dye or other tracer substance is added to the feed while the extruder is operating under nominal conditions. Congealed multiparticulates are then collected over time and analyzed for the dye or tracer substance, from which the mean time is determined.

Generally, atomization occurs in one of several ways, including (1) by "pressure" or single-fluid nozzles; (2) by two-fluid nozzles; (3) by centrifugal or spinning-disk atomizers; (4) by ultrasonic nozzles; and (5) by mechanical vibrating nozzles. Detailed descriptions of atomization processes can be found in Lefebvre, *Atomization and Sprays* (1989) or in *Perry's Chemical Engineers' Handbook*, (7th Ed. 1997). Preferably, a centrifugal or spinning-disk atomizer is used, such as the FX1 100-mm rotary atomizer manufactured by Niro A/S (Soeborg, Denmark).

Once the molten mixture has been atomized, the droplets are congealed, typically by contact with a gas or liquid at a temperature below the solidification temperature of the droplets. Usually, it is desirable that the droplets are congealed in less than about 60 seconds, preferably in less than about 10 seconds, and more preferably in less than about 1 second. Often, congealing at ambient temperature results in sufficiently rapid solidification of the droplets to form suitable multiparticulates. However, the congealing step often occurs in an enclosed space to simplify collection of the multiparticulates. In such cases, the temperature of the congealing media (either gas or liquid) will increase over time as the droplets are introduced into the enclosed space. Thus, a cooling gas or liquid is often circulated through the enclosed space to maintain a constant congealing temperature. For some processes, the cooling gas or liquid can be cooled to below ambient temperature to promote rapid congealing. Suitable thermal-based processes are disclosed in further detail in commonly assigned U.S. patent application Ser. No. 60,527, 244 ("Improved Azithromycin Multiparticulate Dosage Forms by melt-Congeal Processes," and Ser. No. 60/527,315 ("Extrusion Processes for Forming Chemically Stable Drug Multiparticulates," filed concurrently herewith.

A mobility-enhancing agent may be incorporated into the multiparticulates during the thermal-based process. In one preferred method, the mobility-enhancing agent may be mixed with a preblend feed comprising the drug and one or more carriers; the mixture of drug, one or more carriers, and mobility-enhancing agent may then be fed to an extruder used to form a molten mixture that subsequently is formed into multiparticulates, as described above. The conditions for forming the multiparticulates are selected such that a portion of the mobility-enhancing agent remains in the multiparticulates following formation. For example, if the mobility-enhancing agent is water or ethanol, the temperature for forming the multiparticulates is maintained sufficiently low such that a sufficient portion of the added water or ethanol remains in the multiparticulates. Alternatively, the multiparticulate formulation process is conducted in an atmosphere with a sufficient level of water vapor or ethanol vapor to prevent an unacceptably high loss of water or ethanol. The multiparticulates may then optionally be heated as described above to further stabilize their dissolution performance.

In another preferred method, a mobility-enhancing agent may be injected directly into an extruder used to form a molten feed comprising the drug and carrier. As described above, the conditions for forming the multiparticulates are selected such that a sufficient portion of the mobility-enhancing agent is retained in the multiparticulates, which can then optionally be post-treated by heating.

In another aspect, the multiparticulates are made by a liquid-based process comprising the steps of (a) forming a mixture comprising drug, a pharmaceutically acceptable carrier, and a liquid; (b) forming particles from the mixture of step (a); and (c) removing a substantial portion of the liquid from the particles of step (b) to form multiparticulates. Preferably, step (b) is a method selected from (i) atomization of the mixture, (ii) coating seed cores with the mixture, (iii) wet-granulating the mixture, and (iv) extruding the mixture into a solid mass followed by spheronizing or milling the mass.

Preferably, the liquid has a boiling point of less than about 150° C. Examples of liquids suitable for formation of multi-particulates using liquid-based processes include water; alcohols, such as methanol, ethanol, various isomers of propanol and various isomers of butanol; ketones, such as acetone, methyl ethyl ketone and methyl isobutyl ketone; hydrocarbons, such as pentane, hexane, heptane, cyclohexane, methylcyclohexane, octane and mineral oil; ethers, such as methyl tert-butyl ether, ethyl ether and ethylene glycol monoethyl ether; chlorocarbons, such as chloroform, methylene dichloride and ethylene dichloride; tetrahydrofuran; dimethylsulfoxide; N-methylpyrrolidinone; N,N-dimethylacetamide; acetonitrile; and mixtures thereof.

In one embodiment, the particles are formed by atomization of the mixture using an appropriate nozzle to form small droplets of the mixture, which are sprayed into a drying chamber where there is a strong driving force for evaporation of the liquid, to produce solid, generally spherical particles. The strong driving force for evaporation of the liquid is generally provided by maintaining the partial pressure of liquid in the drying chamber well below the vapor pressure of the liquid at the temperature of the particles. This is accomplished by (1) maintaining the pressure in the drying chamber at a partial vacuum (e.g., 0.01 to 0.5 atm); or (2) mixing the droplets with a warm drying gas; or (3) both (1) and (2). Spray-drying processes and spray-drying equipment are described generally in *Perry's Chemical Engineers' Handbook*, pages 20-54 to 20-57 (6th Ed. 1984).

In another embodiment, the particles are formed by coating the liquid mixture onto seed cores. The seed cores can be made from any suitable material such as starch, microcrystalline cellulose, sugar or wax, by any known method, such as melt- or spray-congealing, extrusion/spheronization, granulation, spray-drying and the like.

The liquid mixture can be sprayed onto such seed cores using coating equipment known in the pharmaceutical arts, such as pan coaters (e.g., Hi-Coater available from Freund Corp. of Tokyo, Japan, Accela-Cota available from Manesty of Liverpool, U.K.), fluidized bed coaters (e.g., Würster coaters or top-spray coaters, available from Glatt Air Technologies, Inc. of Ramsey, N.J. and from Niro Pharma Systems of Bubendorf, Switzerland) and rotary granulators (e.g., CF-Granulator, available from Freund Corp).

In another embodiment, the liquid mixture may be wet-granulated to form the particles. Granulation is a process by which relatively small particles are built up into larger granular particles, often with the aid of a carrier, also known as a binder in the pharmaceutical arts. In wet-granulation, a liquid is used to increase the intermolecular forces between particles, leading to an enhancement in granular integrity, referred to as the "strength" of the granule. Often, the strength of the granule is determined by the amount of liquid that is present in the interstitial spaces between the particles during the granulation process. This being the case, it is important that the liquid wet the particles, ideally with a contact angle of zero. Examples of liquids found to be effective wet-granulation liquids include water, ethanol, isopropyl alcohol and acetone.

Several types of wet-granulation processes can be used to form drug-containing multiparticulates. Examples include fluidized bed granulation, rotary granulation and high-shear mixers. In fluidized bed granulation, air is used to agitate or "fluidize" particles of drug and/or carrier in a fluidizing chamber. The liquid is then sprayed into this fluidized bed, forming the granules. In rotary granulation, horizontal discs rotate at high speed, forming a rotating "rope" of drug and/or carrier particles at the walls of the granulation vessel. The liquid is sprayed into this rope, forming the granules. High-shear mixers contain an agitator or impeller to mix the particles of drug and/or carrier. The liquid is sprayed into the moving bed of particles, forming granules. In these processes, all or a portion of the carrier can be dissolved into the liquid prior to spraying the liquid onto the particles. Thus, in these processes, the steps of forming the liquid mixture and forming particles from the liquid mixture occur simultaneously.

In another embodiment, the particles are formed by extruding the liquid mixture into a solid mass followed by spheronizing or milling the mass. In this process, the liquid mixture, which is in the form of a paste-like plastic suspension, is extruded through a perforated plate or die to form a solid mass, often in the form of elongated, solid rods. This solid mass is then milled to form the multiparticulates. In one embodiment, the solid mass is placed, with or without an intervening drying step, onto a rotating disk that has protrusions that break the material into multiparticulate spheres, spheroids, or rounded rods. The so-formed multiparticulates are then dried to remove any remaining liquid. This process is sometimes referred to in the pharmaceutical arts as an extrusion/spheronization process.

Once the particles are formed, a portion of the liquid is removed, typically in a drying step, thus forming the multiparticulates. Preferably, at least 80% of the liquid is removed from the particles, more preferably at least 90%, and most preferably at least 95% of the liquid is removed from the particle during the drying step.

Suitable liquid-based processes are disclosed in further detail in commonly assigned U.S. patent application Ser. No. 60/527,405 ("Improved Azithromycin Multiparticulate Dosage Forms by Liquid-Based Processes," filed concurrently herewith.

A mobility-enhancing agent may be incorporated into multiparticulates made by a liquid-based process. In one such exemplary process, the mobility-enhancing agent may be blended with a drug, one or more carriers, and a liquid to form a mixture. Particles are then formed from the mixture, and the liquid subsequently removed to form the multiparticulates, as described above. Processing conditions are chosen so as to ensure that a portion of the mobility-enhancing agent is retained in the multiparticulates following formation; the multiparticulates may then optionally be heated to further improve stability.

The multiparticulates may also be made by a granulation process comprising the steps of (a) forming a solid mixture comprising a drug and a pharmaceutically acceptable carrier; and (b) granulating the solid mixture to form multiparticulates. Examples of such granulation processes include dry granulation and melt granulation, well known in the art. See, for example, Remington's Pharmaceutical Sciences (18th Ed. 1990).

An example of a dry granulation process is roller compaction, where the solid mixture is compressed between rollers. The rollers can be designed so that the resulting compressed material is in the form of small beads or pellets of the desired diameter. Alternatively, the compressed material is in the form of a ribbon that may be milled to form multiparticulates using methods well known in the arts. See Remington's Pharmaceutical Sciences (16th Ed. 1980).

In melt granulation processes, the solid mixture is fed to granulator that has the capability of heating or melting the carrier. Equipment suitable for use in this process includes high-shear granulators and single or multiple screw extruders such as those described above for melt-congeal processes. In melt granulation processes, the solid mixture is placed into the granulator and heated until the solid mixture agglomerates. The solid mixture is then kneaded or mixed until the desired particle size is attained. The so-formed granules are then cooled, removed from the granulator and sieved to the desired size fraction, thus forming the multiparticulates.

Improved Stability

In addition to increasing the crystallinity of the drug in the multiparticulate, in one embodiment the post-treatment process is conducted for a time sufficiently long to allow the multiparticulates to reach a sufficiently stable, low-energy state. Thus, multiparticulates post-treated by the process of the present invention have improved stability relative to control multiparticulates of essentially the same composition but not post-treated by the process of the present invention. The multiparticulates may exhibit any or all of the following improvements in stability: (1) physical, meaning either (a) the fraction of drug in its lowest energy crystalline state or the fraction of drug in the crystalline state that the drug was in prior to formation of the multiparticulates in the post-treated multiparticulate is greater than that in the control, (b) the rate of change in the crystalline state of the drug and/or carrier in the post-treated multiparticulate is lower than the rate of change in the control multiparticulate, or (c) both (a) and (b); or (2) chemical, meaning a reduction in the degradation or reaction rate of the drug; or (3) dissolution performance-related, meaning a reduction in the rate of change in the dissolution performance of the drug.

Improvement in physical stability may be determined by comparing the crystallinity of the drug in a post-treated multiparticulate, with the crystallinity of drug in the control multiparticulate.

Often, the drug can exist in more than one crystal form. In such cases, one form, or polymorph, is usually preferred over other forms. Often, the lowest energy form is desired because it is the most physically and chemically stable. In some cases, the initial form of the drug prior to forming the multiparticulates is the desired form. For example, normally, for azithromycin, the crystalline dihydrate form is preferred. In such cases, the post-treatment process may provide an increase in the fraction of drug present in the multiparticulates in the lowest-energy crystalline form or an increase in the fraction of drug present in the initial crystalline form. A relative degree of improvement in drug crystal form may be used to measure improvements in this aspect of the invention. By "relative degree of improvement in drug crystal form" is meant the ratio of (1) the amount of drug not in the desired crystal form in a control multiparticulate to (2) the amount of drug not in the desired crystal form in a post-treated multiparticulate. For example, if the amount of lowest energy crystalline drug form in the control multiparticulate is 80 wt % and the amount of lowest energy crystalline drug form in the post-treated multiparticulate is 90 wt %, the relative degree of improvement in crystallinity is (100 wt %-80 wt %)/(100 wt %-90 wt %)=20 wt %/10 wt %=2.0. Similarly, if the amount of drug present as the initial crystalline drug form in the control multiparticulate is 80 wt % and the amount of initial crystalline drug form in the post-treated multiparticulate is 90 wt %, the relative degree of improvement in drug crystal form is (100 wt %-80 wt %)/(100 wt %-90 wt %)=20 wt %/10 wt %=2.0.

A composition is within the scope of this aspect of the invention if the post-treatment process results in a relative degree of improvement in drug crystal form, as determined by one or more of the above methods, of at least 1.25, preferably at least 1.5, and more preferably at least 2.0.

Alternatively, an improvement in physical stability may be determined by comparing the rate of change in the crystalline state of the drug or carrier in a post-treated multiparticulate, with the rate of change in the crystalline state of the drug or carrier in a control multiparticulate. The inventors have found that during the post-treatment process, the crystalline state of the drug or carrier will change to a lower energy state. After reaching the lower-energy state, changes in the drug or carrier form occur much more slowly. For non-post-treated multiparticulates, the transition to a lower-energy state occurs throughout the storage interval. As a result, the rate of change in crystalline state of the drug or carrier will be slower for a post-treated multiparticulate than for a control multiparticulate.

Such changes in the crystalline state of the drug or carrier can be measured by any standard physical measurement, such as PXRD, DSC, solid state NMR or Scanning Electron Microscope ("SEM") analysis, preferably by the PXRD method outlined above. Preferably, the rate of change in crystalline state of the drug or carrier in the post-treated multiparticulate is less than 80%, and more preferably less than 67%, of the rate of change in the control multiparticulate. Thus, for example, if the carrier in the control multiparticulate changes from a high-energy polymorph to a low-energy polymorph at a rate of 30% per year, the carrier in the post-treated multiparticulate will change at a rate of less than 24% per year, preferably less than 20% per year. Often, much more dramatic improvements are observed, such as less than about 10% of the rate of change in the control multiparticulate, or less than about 3% per year for the example given.

Thus, another method for determining the improvement in physical stability of a multiparticulate is to determine the relative degree of improvement in change in crystalline state for the multiparticulate, meaning the ratio of (1) the rate of change of crystalline state of the drug or carrier in a control multiparticulate to (2) the rate of change of crystalline state of the drug or carrier in a post-treated multiparticulate. For example, where the rate of change in crystalline state of a carrier in the post-treated multiparticulate is 4 wt % per year, and the rate of change in crystalline state of a carrier in the control multiparticulate is 5 wt % per year, the relative degree of improvement is 5/4, or 1.25. Preferably, the relative degree of improvement in change in crystalline state is at least 1.25, preferably at least 1.5, and more preferably 2.

In another aspect of the invention, the drug in the post-treated multiparticulate has improved chemical stability compared with drug in a control multiparticulate. The post-treated and control multiparticulates are the same as noted above for physical stability. As used herein, "chemical stability" refers to the rate of chemical degradation of the drug in a typical storage environment. Types of chemical degradation reactions that may occur include, but are not limited to, hydrolysis, lactonization, esterification, oxidation, reduction, ring cyclization, and transesterification. Drug in a chemically stable post-treated multiparticulate has a reduced rate of degradation relative to drug in the control multiparticulate.

In general, drug degradation may be measured using any conventional method for measuring the purity or potency of drug in a pharmaceutical composition. For example, the amount of active drug present in a multiparticulate may be initially measured using high-performance liquid chromatography (HPLC) or other analytical techniques well known in the art. Alternatively, the amount of drug initially present may be calculated from the amount of drug present in the multiparticulate formulation. The potency of the multiparticulate is then measured after storage at controlled temperature and humidity conditions for an appropriate period of time. A decrease in potency indicates that a chemical reaction has occurred, leading to a decrease in the amount of active drug present in the multiparticulate, and is an indication of poor chemical stability.

An alternative method used to evaluate chemical stability is to analyze the rate of increase in the amount of drug degradant(s) in the multiparticulate, which would indicate reaction of the drug. An HPLC or other analytical technique may be used to determine the concentration of drug degradant(s) in a multiparticulate. The amount of the degradant(s) is measured before and after storage under controlled storage conditions. The amount of increase in the drug degradant(s) may be used to determine the amount of decrease in "percent drug purity," defined as 100 times the total amount of drug present divided by the amount of drug initially present. Thus, percent drug purity may be calculated as follows:

$$\text{percent drug purity} = 100 \times \left(\frac{\text{total drug present}}{\text{drug initially present}}\right)$$

When the drug purity is calculated from the total amount of impurities, percent drug purity may be calculated by assuming that the drug initially present, given in wt %, is equal to 100 wt % minus the wt % of total initial impurities, and that total drug present is equal to 100 wt % minus the wt % of total impurities after storage, that is, at some later time. This method of calculating percent drug purity is by the formula:

$$\text{percent drug purity} = 100 \times \left[1 - \left[\frac{\text{total impurities}}{\text{drug initially present}}\right]\right]$$

The rate at which drug degradation occurs is generally dependent on the storage conditions. The drug, when formulated in a multiparticulate of the present invention, should be stable at ambient temperature and humidity conditions (e.g., 20% to 60% RH) for long periods of time, such as months or years. However, to expedite testing, the storage conditions may employ elevated temperature and/or humidity to simulate longer storage times at ambient conditions. The storage time may vary from a few days to weeks or months, depending on the reactivity of the drug and the storage conditions.

A "degree of degradation" of drug following storage may be determined by subtracting the final percent drug purity (determined either by measuring the decrease in drug present or the increase in drug impurities present) from the initial percent drug purity. For example, a sample of multiparticulates initially containing 100 mg drug and having no measurable impurities would have an initial percent drug purity of 100 wt %. If, after storage, the amount of drug in the sample decreases to 95 mg, the final percent drug purity would be 95 wt % and the degree of degradation would be 100 wt % less 95 wt %, or 5 wt %. Alternatively, if 100 mg of drug substance were found to initially have 1 mg of impurities present, it would have an initial percent drug purity of 99 wt %. If, after storage, the total impurities present had increased to 6 wt %, the final percent drug purity would be 94 wt % and the degree of degradation would be 99 wt % less 94 wt %, or 5 wt %.

Alternatively, degree of degradation can be determined by subtracting the amount of one or more specific drug degradants initially present from the amount of that specific degradant present after storage. Such a measure is useful where there are several drug degradants, of which only one or a few is of concern. For example, if a drug initially contained a specific degradant at a concentration of 1 wt % and after storage the concentration of that degradant was 6 wt %, the degree of degradation would be 6 wt % less 1 wt %, or 5 wt %.

A relative degree of improvement in chemical stability may be determined by taking the ratio of the degree of degradation of the drug in a control multiparticulate and the degree of degradation of the drug in a post-treated multiparticulate under the same storage conditions for the same storage time period. For example, where the degree of degradation of a drug in the post-treated multiparticulate is 1 wt %, and the degree of degradation of the control multiparticulate is 50 wt %, the relative degree of improvement is 50 wt %-1 wt %, or 50. For multiparticulates of this aspect of the invention, the relative degree of improvement is at least 1.25. When the drug is particularly unstable, larger relative degrees of improvement may be necessary in order for the chemical stability of the multiparticulate to be pharmaceutically acceptable. In such cases, the invention provides greater chemical stability when the relative degree of improvement is at least about 2, preferably at least about 5, and most preferably at least 10. In fact, some multiparticulates may achieve a relative degree of improvement in chemical stability of greater than 100.

The particular storage conditions and time of storage for testing may be chosen as convenient depending on the stability of the drug, the particular carrier used, and the ratio of drug to carrier in the multiparticulate. Where the drug is particularly unstable, or where the multiparticulate has a low ratio of drug to carrier, then shorter storage time periods may be used. Where the rate of drug degradation is linear, the relative degree of improvement will be independent of the storage time. However, where the rate of drug degradation is non-linear under controlled storage conditions, the stability test used to compare the post-treated multiparticulate with the control multiparticulate is preferably chosen such that the degree of degradation is sufficiently large that it may be accurately measured. Typically, the time period is chosen so as to observe a degree of degradation of at least 0.1 to 0.2 wt %. However, the time period should not be so long that the ratio of drug to carrier changes substantially. Typically, the time period is such that the observed degree of degradation for the post-treated multiparticulate is less than 50 wt % and preferably less than 20 wt %. When the rate of drug degradation in the control multiparticulate is relatively slow, the test is preferably conducted over a long enough period of time under controlled storage conditions to allow a meaningful comparison of the stability of the post-treated multiparticulate with the control multiparticulate.

The drug in the post-treated multiparticulate may have a degree of degradation of less than about 5 wt %, preferably less than about 1 wt %, more preferably less than about 0.5 wt %, and most preferably less than about 0.1 wt % when stored at 40° C. and 75% RH for six months; or less than about 5 wt %, preferably less than about 1 wt %, more preferably less than about 0.5 wt %, and most preferably less than about 0.1 wt %, when stored at 30° C. and 60% RH for one year; or less than about 5 wt %, preferably less than about 1 wt %, more preferably less than about 0.5 wt %, and most preferably less than about 0.1 wt % when stored at ambient conditions for two years or at 25° C. and 60% RH for 2 years. Notwithstanding these preferred degrees of degradation, the multiparticulates of the invention may have a degree of degradation that is much greater than the preferred values, so long as the post-treated multiparticulates achieve the degree of improvement relative to control multiparticulates as described above.

In another aspect of the invention, the compositions of the invention have improved stability in dissolution performance. This may be determined by comparing the rate of change in dissolution performance of drug in a post-treated multiparticulate with the rate of change in dissolution performance of drug in a control multiparticulate. First, following formation of the multiparticulates, the dissolution performance of post-treated multiparticulates and control multiparticulates is determined for at least two time points that are spaced sufficiently far apart as to observe a change in performance in the control multiparticulate and to define a time period. Such a time period is typically at least one day and more typically 1-12 weeks. Storage periods may be up to 2 years. The dissolution performance may compare either the dissolution rate constant (as defined below), or the amount of drug released after a specified period of time. A percentage change in dissolution performance is calculated based on the dissolution performance at the two time points. For example, if a post-treated multiparticulate initially provides a first-order dissolution rate constant at time 0 of 0.010 $min^{-1}$ and one year later provides a dissolution rate constant of 0.008 $min^{-1}$, the percentage change in dissolution performance would be [(0.010 $min^{-1}$-0.008 $min^{-1}$)÷0.01 $min^{-1}$)]×100, or 20%. Likewise, if the post-treated multiparticulate initially released 50% of the drug at 30 minutes and, one year later, released 40% of the drug at 30 minutes, the percentage change in dissolution performance would be [(50%-40%)/50%]×100, or 20%.

A relative degree of improvement in dissolution performance stability may be determined by taking the ratio of the percentage change in dissolution performance of the control multiparticulate and the percentage change in dissolution performance of the post-treated multiparticulate under the same storage conditions for the same storage time period. For example, where the percentage change in dissolution performance of the control multiparticulate is 20%, and the percentage change in dissolution performance of the post-treated multiparticulate is 10%, the relative degree of improvement in dissolution performance is 20%÷10%, or 2. For a multiparticulate of this aspect of the present invention, the relative degree of improvement in dissolution performance stability is at least 1.25. The relative degree of improvement in dissolution performance may be greater than 2, or may be even greater than 4.

The particular storage conditions and time of storage to evaluate physical, chemical, or dissolution performance stability may be chosen as is convenient. A stability test which may be used to test whether a composition meets the stability criteria described above is storage of the post-treated multiparticulate and the control multiparticulate for three weeks at 40° C. and 75% RH. A relative degree of improvement may become apparent within a shorter time, such as three to five days, and shorter storage times may be used for some drugs. When comparing compositions under storage conditions that approximate ambient conditions, e.g., 25° C. and 60% RH, the storage period may need to be from several months up to two years.

Drugs

The multiparticulates of the present invention include a drug. Preferably, the drug makes up at least 10 wt % of the total weight of the multiparticulate, more preferably at least 20 wt %, and most preferably at least 40 wt %. The term "drug" as used herein includes, by way of example and not of limitation, any physiologically or pharmacologically active substance that produces a localized or systemic effect in animals. The term "animals" is meant to include mammals, including human beings as well as other animals.

Examples of drugs employed in the devices of this invention include, without limitation, inorganic and organic compounds that act on the peripheral nerves, adrenergic receptors, cholinergic receptors, nervous system, skeletal muscles, cardiovascular smooth muscles, blood circulatory system, synaptic sites, neuroeffector junctional sites, endocrine and hormone systems, immunological system, reproductive system, autocoid systems, alimentary and excretary systems, inhibitors of autocoids and histamine systems. Preferred classes of drugs include, but are not limited to, antihypertensives, anti-anxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, anti-incontinence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesterol ester transfer protein inhibitors.

Each named drug should be understood to include the neutral form of the drug and pharmaceutically acceptable forms thereof. By "pharmaceutically acceptable forms" thereof is meant any pharmaceutically acceptable derivative or variation, including stereoisomers, stereoisomer mixtures, enantiomers, solvates, hydrates, isomorphs, polymorphs, salt forms and prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin and atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4', 6'-trimethylphenoxy)pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin, amoxicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid, quinapril, and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesterol ester transfer protein inhibitors include [2R,4S]-4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S]-4-[3,5-bis-trifluoromethyl-benzyl)-methoxycarbonyl-amino]-2-ethyl-6-trifluoromethyl-3,4-dihydro-2H-quinoline-1-carboxylic acid ethyl ester, and [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester.

A preferred drug for use with the present invention is azithromycin. Azithromycin is the generic name for the drug 9a-aza-9a-methyl-9-deoxo-9a-homoerythromycin A, a broad-spectrum antimicrobial compound derived from erythromycin A. Accordingly, azithromycin and certain derivatives thereof are useful as antibiotics. The drug may be in the form of the free base, a pharmaceutically acceptable salt or a prodrug. The drug may also be in its anhydrous, hydrated or solvated forms. The invention is intended to encompass all such forms. The azithromycin present in the multiparticulates of the present invention is preferably crystalline, including any crystalline polymorphs. The various polymorphs of crystalline azithromycin are disclosed in commonly assigned pending patent application Publication No. 20030162730, published Aug. 28, 2003; U.S. Pat. Nos. 6,365,574 and 6,245, 903; U.S. patent application Publication Nos. 20010047089, published Nov. 29, 2001, and 20020111318, published Aug. 15, 2002; and International Application Publication Nos. WO 01/00640, WO 01/49697, WO 02/10181 and WO 02/42315. In a preferred embodiment, the azithromycin is in the form of the crystalline dihydrate, described in U.S. Pat. No. 6,268, 489.

Carriers

The multiparticulates made by the process of the present invention include a pharmaceutically acceptable carrier. By "pharmaceutically acceptable" is meant the carrier must be compatible with the other ingredients of the composition, and not deleterious to the recipient thereof. Generally, the carrier is selected to keep degradants to acceptable levels. The carrier functions as a matrix for the multiparticulate or to affect the rate of release of drug from the multiparticulate, or both. The carrier may consist of a single material, or may be a mixture or blend of materials.

Examples of carriers suitable for use in the multiparticulates of the present invention include long-chain alcohols, such as stearyl alcohol, cetyl alcohol, and polyethylene glycol; long-chain fatty acid esters, such as glyceryl monooleate, glyceryl monostearate, glyceryl palmitostearate, polyethoxylated castor oil derivatives, hydrogenated vegetable oils, mono-, di-, and tri-alkyl glycerides, and glyceryl mono-, di-, and tri-behenates; waxes, such as synthetic wax, microcrystalline wax, paraffin wax, carnauba wax, and white and yellow beeswax; ether-substituted cellulosics, such as microcrystalline cellulose, hydroxypropyl cellulose, hydroxypropyl methyl cellulose, and ethylcellulose; ester-substituted cellulosics, such as cellulose acetate, cellulose acetate phthalate, hydroxypropyl methyl cellulose phthalate, cellulose acetate trimellitate, and hydroxypropyl methyl cellulose acetate succinate; and acid- or ester-functionalized polymethacrylates and polyacrylates. Mixtures and blends of such materials may also be used.

Carriers used in the multiparticulates made by the present invention will generally make up about 10 wt % to about 95 wt % of the multiparticulate, preferably about 20 wt % to about 90 wt % of the multiparticulate, and more preferably about 40 wt % to about 70 wt % of the multiparticulates, based on the total mass of the multiparticulate. The carriers are preferably solid at temperatures of about 40° C. The inventors have found that if the carrier is not a solid at 40° C., there can be changes in the physical characteristics of the composition over time, especially when stored at elevated temperatures, such as at 40° C. Thus, it is preferred that the carrier be a solid at a temperature of about 50° C., more preferably about 60° C.

Optional Excipients

The multiparticulates may optionally include excipients to aid in forming the multiparticulates, to affect the release rate of azithromycin from the multiparticulates, or for other purposes known in the art.

The multiparticulates may optionally include a dissolution enhancer. Dissolution enhancers increase the rate of dissolution of the drug from the carrier. In general, dissolution enhancers are amphiphilic compounds and are generally more hydrophilic than the carrier. Dissolution enhancers will generally make up about 0.1 to about 30 wt % of the total mass of the multiparticulate. Exemplary dissolution enhancers include alcohols such as stearyl alcohol, cetyl alcohol, and polyethylene glycol; surfactants, such as poloxamers (such as poloxamer 188, poloxamer 237, poloxamer 338, and poloxamer 407), docusate salts, polyoxyethylene alkyl ethers, polyoxyethylene castor oil derivatives, polysorbates, polyoxyethylene alkyl esters, sodium lauryl sulfate, and sorbitan monoesters; sugars such as glucose, sucrose, xylitol, sorbitol, and maltitol; salts such as sodium chloride, potassium chloride, lithium chloride, calcium chloride, magnesium chloride, sodium sulfate, potassium sulfate, sodium carbonate, magnesium sulfate, and potassium phosphate; amino acids such as alanine and glycine; and mixtures thereof. While not wishing to be bound by any particular theory or mechanism, it is believed that dissolution-enhancers present in the multiparticulates affect the rate at which the aqueous use environment penetrates the multiparticulate, thus affecting the rate at which drug is released. In addition, such agents may enhance the drug release rate by aiding in the aqueous dissolution of the carrier itself, often by solubilizing the carrier in micelles. Preferably, the dissolution enhancer is a surfactant, and most preferably, the dissolution enhancer is a poloxamer.

Agents that inhibit or delay the release of drug from the multiparticulates can also be included in the carrier. Such dissolution-inhibiting agents are generally hydrophobic. Examples of dissolution-inhibiting agents include: dialkylphthalates such as dibutyl phthalate, hydrocarbon waxes, such as microcrystalline and paraffin wax; and polyethylene glycols having molecular weights greater than about 20,000 daltons.

Another useful class of excipients, especially when the multiparticulates are made via thermal-based processes, is materials that are used to adjust the viscosity of the molten mixture used to form the multiparticulates. Such viscosity-adjusting excipients will generally make up 0 to 25 wt % of the multiparticulate, based on the total mass of the multiparticulate. The viscosity of the molten mixture is a key variable in obtaining multiparticulates with a narrow particle size distribution. For example, when a spinning-disc atomizer is employed, it is preferred that the viscosity of the molten mixture be at least about 1 cp and less than about 10,000 cp, more preferably at least 50 cp and less than about 1000 cp. If the molten mixture has a viscosity outside these preferred ranges, a viscosity-adjusting carrier can be added to obtain a molten mixture within the preferred viscosity range. Examples of viscosity-reducing excipients include stearyl alcohol, cetyl alcohol, low molecular weight polyethylene glycol (e.g., less than about 1000 daltons), isopropyl alcohol, and water. Examples of viscosity-increasing excipients include microcrystalline wax, paraffin wax, synthetic wax, high molecular weight polyethylene glycols (e.g., greater than about 5000 daltons), ethyl cellulose, hydroxypropyl cellulose, hydroxypropyl methyl cellulose, methyl cellulose, silicon dioxide, microcrystalline cellulose, magnesium silicate, sugars, and salts.

Other excipients may be added to adjust the release characteristics of the multiparticulates or to improve processing and will typically make up 0 to 50 wt % of the multiparticulate, based on the total mass of the multiparticulate. For example, for basic drugs, such as azithromycin, solubility in aqueous solution decreases with increasing pH; therefore, a base may be included in the composition to decrease the rate at which the drug is released in an aqueous use environment. Examples of bases that can be included in the composition include di- and tri-basic sodium phosphate, di- and tri-basic calcium phosphate, mono-, di-, and tri-ethanolamine, sodium bicarbonate, sodium citrate dihydrate, and amine-functionalized methacrylate polymers and copolymers, such as EUDRAGIT E100® from Rohm GmbH as well as other oxide, hydroxide, phosphate, carbonate, bicarbonate and citrate salts, including hydrated and anhydrous forms known in the art. Still other excipients may be added to reduce the static charge on the multiparticulates; examples of such anti-static agents include talc and silicon dioxide. Flavorants, colorants, and other excipients may also be added in their usual amounts for their usual purposes.

In one embodiment, the carrier and one or more optional excipients form a solid solution, meaning that the carrier and one or more optional excipients form a single thermodynamically stable phase. When a thermal-based process, such as melt-congealing, is used to form the multiparticulates, the carrier/excipient mixture may be entirely molten at processing temperatures used to form multiparticulates or one material may be solid while the other(s) are molten, resulting in a suspension of one material in the molten mixture.

When the carrier and one or more optional excipients do not form a solid solution but one is desired, for example, to obtain a specific controlled-release profile, a third excipient may be included in the composition to produce a solid solution comprising the carrier, the one or more optional excipients, and the third excipient. For example, it may be desirable to use microcrystalline wax and a surfactant, such as poloxamer, to obtain a multiparticulate with the desired release profile. In such cases a solid solution is not formed, in part due to the hydrophobic nature of the microcrystalline wax and the hydrophilic nature of the poloxamer. By including a small amount of a third component, such as stearyl alcohol, in the formulation, a solid solution can be obtained resulting in a multiparticulate with the desired release profile.

In one aspect, the multiparticulates are in the form of a non-disintegrating matrix. By "non-disintegrating matrix" is meant that at least a portion of the carrier does not dissolve or disintegrate after introduction of the multiparticulates to an aqueous use environment. In such cases, the drug and optionally a portion of one or more optional excipients, for example, a dissolution enhancer, are removed from the multiparticulate by dissolution. At least a portion of the carrier does not dissolve or disintegrate and is excreted when the use environment is in vivo, or remains suspended in a test solution when the use environment is in vitro. In this aspect, it is preferred that at least a portion of the carrier have a low solubility in the aqueous use environment. Preferably, the solubility of the carrier in the aqueous use environment is less than about 1 mg/mL, more preferably less than about 0.1 mg/mL, and most preferably less than about 0.01 mg/ml. Examples of suitable low-solubility carriers include waxes, such as synthetic wax, microcrystalline wax, paraffin wax, carnauba wax, and beeswax; glycerides, such as glyceryl monooleate, glyceryl monostearate, glyceryl palmitostearate, glyceryl mono-, di- or tribehenates, glyceryl tristearate, glyceryl tripalmitate; and mixtures thereof.

In one embodiment, the multiparticulate comprises about 20 to about 75 wt % drug, about 25 to about 80 wt % of a carrier, and about 0.1 to about 30 wt % of a dissolution-enhancer based on the total mass of the multiparticulate.

In a preferred embodiment, the multiparticulate comprises about 35 wt % to about 55 wt % drug; about 40 wt % to about 65 wt % of an excipient selected from waxes, such as synthetic wax, microcrystalline wax, paraffin wax, carnauba wax, and beeswax; glycerides, such as glyceryl monooleate, glyceryl monostearate, glyceryl palmitostearate, polyethoxylated castor oil derivatives, hydrogenated vegetable oils, glyceryl mono-, di- or tribehenates, glyceryl tristearate, glyceryl tripalmitate; and mixtures thereof; and about 0.1 to about 15 wt % of a dissolution-enhancer selected from surfactants, such as poloxamers, polyoxyethylene alkyl ethers, polysorbates, polyoxyethylene alkyl esters, sodium lauryl sulfate, and sorbitan monoesters; alcohols, such as stearyl alcohol, cetyl alcohol, and polyethylene glycol; sugars such as glucose, sucrose, xylitol, sorbitol, and maltitol; salts such as sodium chloride, potassium chloride, lithium chloride, calcium chloride, magnesium chloride, sodium sulfate, potassium sulfate, sodium carbonate, magnesium sulfate, and potassium phosphate; amino acids such as alanine and glycine; and mixtures thereof.

In another embodiment, the multiparticulates of the present invention comprise (a) a drug; (b) a glyceride carrier having at least one alkylate substituent of 16 or more carbon atoms; and (c) a polyoxyethylene-polyoxypropylene block copolymer (poloxamer). At least 70 wt % of the drug in the multiparticulate is crystalline. Small changes in the relative amounts of the glyceride carrier and the poloxamer result in large changes in the release rate of the drug. This allows the release rate of the drug from the multiparticulate to be precisely controlled by selecting the proper ratio of drug, glyceride carrier and poloxamer. These carriers have the further advantage of releasing nearly all of the drug from the multiparticulate. Such multiparticulates are disclosed more fully in commonly assigned U.S. patent application Ser. No. 60/527,329 ("Multiparticulate Crystalline Drug Compositions Having Controlled Release Profiles," filed concurrently herewith.

Drug Release Rate

The term "drug release rate" as used herein means the profile or curve obtained by plotting the amount of drug released from a sample of multiparticulates versus time following introduction to an aqueous use environment. The multiparticulates of the present invention may be designed for immediate release, controlled release, delayed release or any combination of these or for exhibiting release profiles between these three types of release. Generally, the rate of release of drug from a multiparticulate will depend on several factors, including the composition of the multiparticulate, the diameter of the multiparticulate, and the pH of the use environment.

For some controlled release formulations, the rate of release of drug from the multiparticulates can be characterized by a first-order dissolution rate constant k. This dissolution rate constant can be determined by fitting a plot of the amount of drug released from a sample over time to the following first-order equation I:

$$A_t = A_\infty \cdot [1 - e^{-kt}] \qquad (I)$$

where $A_t$ is the percentage of drug released from the multiparticulates at time t, $A_\infty$ is the percentage of drug released from the multiparticulates over long periods of time, generally in excess of three hours, t is the elapsed time of dissolution of drug in minutes, and k is the drug dissolution rate constant in $\text{min}^{-1}$.

For some delayed release formulations, the rate of release of drug can be characterized by two parameters: (1) a "lag time," defined as the time between introduction of the multiparticulate to the use environment and the time the drug begins releasing from the multiparticulate, and (2) a first-order dissolution rate constant describing the drug's release rate after the lag time. In this case, the dissolution rate constant can be determined by fitting a plot of the amount of drug released from a sample over time to the following delayed release first-order equation II:

$$A_t = A_\infty \cdot [1 - e^{-k(t-\tau)}] \quad \text{(II)}$$

Where τ is the lag time in minutes, and the other symbols are as defined in Equation I.

Other equations known in the art can also be used to describe the rate of release of drugs from multiparticulates. Such equations often require the fitting of the data so that one or more constants that describe the drug release rate can be determined.

The dissolution rate of drug from a multiparticulate may also be characterized by the amount released at a specified time following introduction of the multiparticulate to a use environment. The specified time may be selected as convenient for determining the release rate of drug from the multiparticulate. Typically, times such as 30 minutes or 60 minutes are selected for determining the amount released from the multiparticulate. To determine the amount released, the multiparticulates are introduced to an aqueous environment of use and the use environment sampled at the selected time and analyzed for the amount of drug released into the solution by analytical methods known in the art, such as high-performance liquid chromatograph (HPLC) analysis. The amount released may be reported as the mass of drug released, the fraction or percentage of drug initially present in the multiparticulate released, or some other convenient measure of the amount of drug released.

The dissolution rate of drug from a multiparticulate may also be characterized by the time required for half of the drug to be released from the multiparticulate following introduction to a use environment. This value, $t_{1/2}$, may be determined by measuring the amount of drug released versus time following introduction to an aqueous environment of use using methods known in the art.

As noted above, the aqueous environment of use may be in vivo fluids, such as the GI tract of an animal such as a human, or it may more conveniently be an in vitro test medium, such as a buffer solution. Appropriate test solutions include aqueous solutions at 37° C. comprising (1) 0.1 N HCl, simulating gastric fluid without enzymes; (2) 0.01 N HCl, simulating gastric fluid that avoids excessive acid degradation of acid-sensitive drugs, and (3) 50 mM $KH_2PO_4$, adjusted to pH 6.8 using KOH or 50 mM $Na_3PO_4$, adjusted to pH 6.8 using NaOH, both simulating intestinal fluid without enzymes. The inventors have also found that for some formulations, an in vitro test solution comprising 100 mM $Na_2HPO_4$, adjusted to pH 6.0 using NaOH provides a discriminating means to differentiate among different formulations on the basis of dissolution profile. It has been determined that in vitro dissolution tests in such solutions provide a good indicator of in vivo performance and bioavailability. Further details of in vitro tests and test solutions are described herein.

A typical test to determine the drug release rate from the multiparticulates of the present invention can be conducted as follows. Samples of the multiparticulates are placed into a USP Type 2 dissoette flask equipped with Teflon-coated paddles rotating at 50 rpm. The flask contains 750 mL of IB solution held at 37.0±0.5° C. The multiparticulates are pre-wetted with 10 mL of the IB solution before being added to the flask. At each time interval, a 3-mL sample of the fluid in the flask is then collected. The collected sample is filtered using a 0.45-μm syringe filter prior to analyzing via HPLC. The percentage of drug released from the multiparticulates at the time the sample was collected is then determined by dividing the mass of drug in the dissolution flask (determined by multiplying the HPLC-determined concentration by the volume of the dissolution media) by the total mass of drug initially added to the dissolution media.

For example, 3 g of multiparticulates containing 50 wt % of the drug azithromycin may be added to 750 mL of IB solution. Thus, 3 g×0.50 or 1.5 g of azithromycin was initially added to the solution. After 60 minutes, a sample of the solution may be taken and analyzed by HPLC and found to contain 1.0 mg/mL of azithromycin. Thus, at t=60 minutes, the amount of azithromycin released from the multiparticulates was 750 mg or 0.75 g (1 mg/mL×750 mL). Therefore, the percentage of azithromycin released from the multiparticulates at t=60 minutes is 100×(0.75 g released÷1.5 g initially present), or 50%.

The value of $A_\infty$ in equation I can be determined by performing a dissolution test as described above and monitoring the amount of drug released from the multiparticulates over time until no change in the amount of drug released is observed. $A_\infty$ therefore represents the maximum amount of drug that can be released from the multiparticulate.

Since the time required to determine $A_\infty$ will vary depending on the composition of the multiparticulate, it is often more convenient to estimate $A_\infty$ by first measuring the amount of drug released from multiparticulates after a convenient and sufficiently long time, such as 180 minutes (to obtain $A_{180}$), then collecting the multiparticulates from the dissolution flask and placing them in a recovery solution to determine the residual amount of drug remaining in the multiparticulates ($A_{residual}$). $A_\infty$ is then equal to the sum of $A_{180}$ and $A_{residual}$. One method for measuring $A_{residual}$ is to collect the multiparticulates after 180 minutes in a test medium, rinse them, and then place them in a recovery solution for the drug and sonicate them for 30 minutes. An appropriate recovery solution will vary from drug to drug, but typically will comprise any of methanol, ethanol, isopropanol, acetonitrile (ACN), and mixtures thereof and mixtures thereof with water.

Alternatively, an in vitro test known as a gastric buffer-to-intestinal buffer transfer test (GB-IB transfer test), can be used to simulate an in vivo aqueous environment of use. In this test, samples of the multiparticulates are first placed into an appropriate GB solution, such as the one described above. After a predetermined period of time, generally 15 to 120 minutes, a concentrated buffer solution is added to the GB solution, increasing the pH of the solution so that it effectively becomes a simulated IB solution. The amount of drug released from the multiparticulates may then be determined using the procedures outlined above.

Dosage Forms

Multiparticulates are amenable to use in scaling dosage forms according to the weight of an individual animal in need of treatment by simply scaling the mass of particles in the dosage form to comport with the animal's weight. They allow the incorporation of a large quantity of drug into a simple dosage form such as a sachet that can be formulated into a slurry that can easily be consumed orally.

The multiparticulates may be mixed or blended with one or more pharmaceutically acceptable materials to form a suitable dosage form. Suitable dosage forms include tablets, capsules, sachets, oral powders for constitution, and the like.

The invention also provides a method of treating a disease or condition amenable to treatment with a therapeutic drug administered in a multiparticulate dosage form, comprising administering to an animal, including a human, in need of such treatment, a dosage form of the type described herein, the dosage form containing an effective amount of the drug. The amount of drug which is administered will necessarily be varied according to principles well known in the art, taking into account factors such as the severity of the disease or condition being treated and the size and age of the patient. In general, the drug is to be administered so that an effective dose is received, with the effective dose being determined from safe and efficacious ranges of administration already known for the drug of interest.

Other features and embodiments of the invention will become apparent from the following examples, which are given for illustration of the invention, rather than for limiting its intended scope.

EXAMPLES

Twelve batches of drug-containing multiparticulates (MP1-MP12) were prepared by various methods and then post-treated in accordance with the invention to improve their stability.

Multiparticulates MP1

Multiparticulates comprising 50 wt % azithromycin dihydrate in a carrier of 46 wt % glyceryl mono-, di- and tri-behenates (commercially available as COMPRITOL 888 ATO from Gattefossé Corporation of Paramus, N.J.) and 4 wt % poloxamer 407 (of a block copolymer of ethylene and propylene oxides commercially available as PLURONIC F127 or LUTROL F127 from BASF Corporation of Mt. Olive, N.J.) were prepared using the following procedure. A mixture of 2.5 kg azithromycin dihydrate, 2.3 kg of the COMPRITOL 888 ATO and 0.2 kg of the PLURONIC F127 was blended in a V-blender for 20 minutes. This blend was then de-lumped using a Fitzpatrick M5A mill at 3000 rpm, knives forward using a 0.065-inch screen. The blend was then placed back into a V-blender for an additional 20 minutes. Three batches of this blended material were then combined to form a preblend feed.

The preblend feed was delivered to a B&P 19-mm twin-screw extruder (MP19-TC with a 25 L/D ratio purchased from B & P Process Equipment and Systems, LLC, Saginaw, Mich.) at a rate of 140 g/min. The extruder was set so as to produce a molten feed suspension of the azithromycin dihydrate in the carrier at a temperature of about 90° C. The feed suspension was then delivered to the center of a spinning-disk atomizer. The spinning disk atomizer, which was custom made, consists of a bowl-shaped stainless steel disk of 10.1 cm (4 inches) in diameter. The surface of the disk is heated with a thin film heater beneath the disk to about 88-90° C. That disk is mounted on a motor that drives the disk of up to approximately 10,000 RPM. The entire assembly is enclosed in a plastic bag of approximately 8 feet in diameter to allow congealing and to capture multiparticulates formed by the atomizer. Air is introduced from a port underneath the disk to provide cooling of the multiparticulates upon congealing and to inflate the bag to its extended size and shape.

A suitable commercial equivalent, to this spinning disk atomizer, is the FX1 100-mm rotary atomizer manufactured by Niro A/S (Soeborg, Denmark).

The surface of the spinning disk atomizer was maintained at 88 to 90° C., and the disk was rotated at 5500 rpm, while forming the azithromycin multiparticulates.

The maximum residence time of azithromycin in the twin-screw extruder was about 60 seconds, and the total time the azithromycin was exposed to the molten suspension was less than about three minutes.

The mean particle size of the resulting multiparticulates was determined to be 210 μm using a Horiba LA-910 particle-size analyzer. The melting point of the carrier, as measured by DSC analysis, was about 70° C.

Multiparticulates MP2

Multiparticulates were formed as described for Multiparticulates M1, except that a single mixture of 3 kg azithromycin dihydrate, 2.76 kg COMPRITOL 888 ATO, and 0.24 kg of PLURONIC F127 was used to form the preblend feed. The resulting multiparticulates had a mean particle size of 200 μm and 77%±11% of the azithromycin in the multiparticulates was crystalline dihydrate. The melting point of the carrier, as measured by DSC analysis, was about 70° C.

Multiparticulates MP3

Multiparticulates comprising 50.53 wt % azithromycin dihydrate, 45.47 wt % COMPRITOL 888 ATO, and 4.0 wt % PLURONIC F127 were prepared using the following procedure. A mixture of 4.04 kg azithromycin dihydrate, 3.64 kg of the COMPRITOL 888 ATO and 0.32 kg of the PLURONIC F127 was blended in a V-blender for 20 minutes. This blend was then de-lumped using a Fitzpatrick M5A mill at 3000 rpm, knives forward using a 0.065-inch screen. The blend was then placed back into a V-blender for an additional 20 minutes to form a preblend feed.

The preblend feed was delivered to a Leistritz 27-mm twin-screw extruder (Model ZSE 27, American Leistritz Extruder Corporation, Somerville, N.J.) at a rate of about 140 g/min. The extruder was set so as to produce a molten feed suspension of the azithromycin dihydrate in the COMPRITOL 888 ATO/PLURONIC F127 carrier at a temperature of about 90° C. The feed suspension was then delivered to the spinning-disk atomizer used to form Multiparticulates MPI. The surface of the spinning disk atomizer was maintained at 90° C. and the disk was rotating at 5500 rpm.

The resulting multiparticulates had a mean particle size of 210 μm and 78%±3% of the azithromycin in the multiparticulates was crystalline dihydrate. The melting point of the carrier, as measured by DSC analysis, was about 70° C.

Multiparticulates MP4

Multiparticulates were prepared as described for Multiparticulates MP1 except that a single mixture of 2.5 kg azithromycin dihydrate, 2.3 kg of the COMPRITOL 888 ATO and 0.2 kg of the PLURONIC F127 was used to form the preblend feed, the extruder was set so as to produce a molten feed suspension of the azithromycin dihydrate in the COMPRITOL 888 ATO/PLURONIC F127 at a temperature of about 85° C., and the spinning disk atomizer was maintained at 85° C.

The resulting multiparticulates had a mean particle size of 202 μm and 72%±5% of the azithromycin in the multiparticulates was crystalline dihydrate. The melting point of the carrier, as measured by DSC analysis, was about 70° C.

Multiparticulates MP5

Multiparticulates were prepared as described for Multiparticulates MP3, except that the preblend feed comprised 50 wt % azithromycin dihydrate, 45 wt % of the COMPRITOL 888 ATO and 5 wt % of the PLURONIC F127. The resulting multiparticulates had a mean particle size of 205 μm and 84±4% of the azithromycin in the carrier was crystalline dihydrate. The melting point of the carrier, as measured by DSC analysis, was about 70° C.

Multiparticulates MP6

Multiparticulates were prepared as described for Multiparticulates MP3, except that the preblend feed comprised 50.53 wt % azithromycin dihydrate, 45.47 wt % of the COMPRITOL 888 ATO and 4 wt % of the PLURONIC F127 and the disk temperature was maintained at 88 to 89° C. The resulting multiparticulates had a mean particle size of 185 μm and 64±3% of the azithromycin in the carrier multiparticulates was crystalline dihydrate. The melting point of the carrier, as measured by DSC analysis, was about 70° C.

Multiparticulates MP7

Multiparticulates comprising 50 wt % azithromycin dihydrate, 45 wt % COMPRITOL 888 ATO, and 5 wt % PLURONIC F127 were prepared as described for Multiparticulates MPI with the exceptions noted. First, 112.5 g of the COMPRITOL 888 ATO, 12.5 g of the PLURONIC F227 and 2 g of water were added to a sealed, jacketed stainless-steel tank equipped with a mechanical mixing paddle. Heating fluid at 97° C. was circulated through the jacket of the tank. After about 40 minutes, the mixture had melted, having a temperature of about 95° C. This mixture was then mixed at 370 rpm for 15 minutes. Next, 125 g of azithromycin dihydrate that had been pre-heated at 95° C. and 100% RH was added to the melt and mixed at a speed of 370 rpm for 5 minutes, resulting in a feed suspension of the azithromycin dihydrate in the molten components.

The feed suspension was then pumped at a rate of 250 g/min using a gear pump to the center of the spinning-disk atomizer heated to 100° C. and rotating at 7500 rpm. The particles formed by the spinning-disk atomizer were congealed in ambient air and a total of 205 g of multiparticulates collected. The mean particle size was determined to be 170 μm using a Horiba LA-910 particle-size analyzer. Samples of the multiparticulates were also evaluated by PXRD, which showed that 83%±10% of the azithromycin in the multiparticulates was crystalline dihydrate. The melting point of the carrier, as measured by DSC analysis, was about 70° C.

Multiparticulates MP8

Multiparticulates comprising 50 wt % azithromycin dihydrate, 40 wt % COMPRITOL 888 ATO and 10 wt % PLURONIC F127 were prepared as described for Multiparticulates MP1 except that 3 kg of preblend feed was fed to the extruder. Samples of the multiparticulates were evaluated by PXRD and 85%±6% of the azithromycin in the multiparticulates was crystalline dihydrate. The melting point of the carrier, as measured by DSC analysis, was about 70° C.

Multiparticulates MP9

Multiparticulates comprising 50 wt % azithromycin dihydrate, 46 wt % COMPRITOL 888 ATO and 4 wt % PLURONIC F127 were prepared as described for Multiparticulates MP1 except that the temperature of the feed suspension was 85° C. and the surface of the spinning disk atomizer was maintained at 85° C. Samples of the multiparticulates were evaluated by PXRD and 82%±6% of the azithromycin in the multiparticulates was crystalline dihydrate. The melting point of the carrier, as measured by DSC analysis, was about 70° C.

Multiparticulates MP10

Multiparticulates comprising 50 wt % azithromycin dihydrate, 47 wt % COMPRITOL 888 ATO and 3 wt % PLURONIC F127 were made described for Multiparticulates MP1, except that the disk temperature was 86° C., the batch size was 1015 gm, and the feed rate was 180 g/min. In addition, 3.45 wt % water was added to the preblend feed fed to the extruder. Samples of the so-formed multiparticulates were evaluated by PXRD and 94%±6% of the azithromycin in the multiparticulates was crystalline dihydrate. The melting point of the carrier, as measured by DSC analysis, was about 70° C.

Multiparticulates MP11

Multiparticulates were made comprising 50 wt % azithromycin dihydrate, 47 wt % COMPRITOL 888 ATO, and 3 wt % PLURONIC F127 as dissolution enhancer. The melting point of the carrier, as determined by DSC analysis, was about 70° C. First, 15 kg azithromycin dihydrate, 14.1 kg of the COMPRITOL 888 ATO and 0.9 kg of the PLURONIC F127 were weighed and passed through a Quadro 194S Comil mill in that order. The mill speed was set at 600 rpm. The mill was equipped with a No. 2C-075-H050/60 screen (special round), a No. 2C-1607-049 flat blade impeller, and a 0.225-inch spacer between the impeller and screen. The mixture was blended using a Servo-Lift 100-L stainless-steel bin blender rotating at 20 rpm, for a total of 500 rotations, forming a preblend feed.

The preblend feed was delivered to a Leistritz 50 mm twin-screw extruder (Model ZSE 50, American Leistritz Extruder Corporation, Somerville, N.J.) at a rate of 25 kg/hr. The extruder was operated in co-rotating mode at about 300 rpm, and interfaced with a melt/spray-congeal unit. The extruder had nine segmented barrel zones and an overall extruder length of 36 screw diameters (1.8 m). Water was injected into barrel number 4 at a rate of 8.3 g/min. The extruder's rate of extrusion was set such that it produced a molten feed suspension of the azithromycin dihydrate in the COMPRITOL 888 ATO/PLURONIC F127 at a temperature of about 90° C.

The molten feed suspension was then delivered to the spinning-disk atomizer described in connection with Multiparticulates MPI, maintained at 90° C. and rotating at 7600 rpm. The maximum total time the azithromycin was exposed to the molten suspension was less than about 10 minutes. The particles formed by the spinning-disk atomizer were cooled and congealed in the presence of cooling air circulated through the product collection chamber. The mean particle size was determined to be 188 μm using a Horiba LA-910 particle size analyzer. Samples of the multiparticulates were also evaluated by PXRD, which showed that about 99% of the azithromycin in the multiparticulates was in the crystalline dihydrate form.

Multiparticulates MP12

Multiparticulates were made comprising 50 wt % azithromycin dihydrate, 47 wt % COMPRITOL 888 ATO, and 3 wt % LUTROL F127 using the following procedure. First, 140 kg azithromycin dihydrate was weighed and passed through a Quadro Comil 196S with a mill speed of 900 rpm. The mill was equipped with a No. 2C-075-H050/60 screen (special round, 0.075"), a No. 2F-1607-254 impeller, and a 0.225 inch spacer between the impeller and screen. Next, 8.4 kg of the LUTROL F127 and then 131.6 kg of the COMPRITOL 888 ATO were weighed and passed through a Quadro 194S Comil mill. The mill speed was set at 650 rpm. The mill was equipped with a No. 2C-075-R03751 screen (0.075"), a No. 2C-1601-001 impeller, and a 0.225-inch spacer between the impeller and screen. The mixture was blended using a Gallay 38 cubic foot stainless-steel bin blender rotating at 10 rpm for 40 minutes, for a total of 400 rotations, forming a preblend feed.

The preblend feed was delivered to a Leistritz 50 mm twin-screw extruder (Model ZSE 50, American Leistritz Extruder Corporation, Somerville, N.J.) at a rate of about 20 kg/hr. The extruder was operated in co-rotating mode at about 100 rpm, and interfaced with a melt/spray-congeal unit. The extruder had five segmented barrel zones and an overall extruder length of 20 screw diameters (1.0 m). Water was injected into barrel number 2 at a rate of 6.7 g/min (2 wt %). The extruder's rate of extrusion was adjusted so as to produce a molten feed suspension of the azithromycin dihydrate in the COMPRITOL 888 ATO/LUTROL F127 at a temperature of about 90° C.

The feed suspension was delivered to the spinning-disk atomizer described in connection with Multiparticulates MP 1, rotating at 6400 rpm and maintained at a temperature of about 90° C. The maximum total time the azithromycin was exposed to the molten suspension was less than 10 minutes. The particles formed by the spinning-disk atomizer were cooled and congealed in the presence of cooling air circulated through the product collection chamber. The mean particle size was determined to be about 200 μm using a Malvern particle size analyzer. Samples of the multiparticulates were also evaluated by PXRD, which showed that about 81% of the azithromycin in the multiparticulates was in the crystalline dihydrate form.

The rates of drug release for Multiparticulates MP1-MP12 in both intestinal buffer (IB) and gastric buffer (GB) were then determined as noted below.

Drug Release Rate in IB

In the following examples, the drug release rate from the multiparticulates was determined in a simulated IB solution using the following procedure. A 750-mg sample of the multiparticulates was placed into a USP Type 2 dissoette flask equipped with Teflon-coated paddles rotating at 50 rpm. The flask contained 750 mL of IB consisting of 0.05 M $Na_3PO_4$ adjusted to pH 6.8 with NaOH held at 37.0±0.5° C. The multiparticulates were pre-wet with 10 mL of the simulated intestinal buffer before being added to the flask. A 3-mL sample of the fluid in the flask was then collected at various time points following addition of the multiparticulates to the flask. The samples were filtered using a 0.45-μm syringe filter prior to analyzing via HPLC (Hewlett Packard 1100, Waters Symmetry $C_8$ column, 45:30:25 acetonitrile:methanol:25 mM $KH_2PO_4$ buffer at 1.0 mL/min, absorbance measured at 210 nm with a diode array spectrophotometer).

The multiparticulates were then removed from the dissolution flask and placed in a recovery solution consisting of 100 mL acetonitrile (ACN) to which was added 100 mL water. This solution was sonicated for 30 minutes, following which samples were collected, filtered using a syringe filter and then analyzed by HPLC as described above to obtain the amount of residual azithromycin remaining in the multiparticulates.

The drug dissolution rate constant in IB was determined by fitting the data to the following equation:

$$A_t = A_\infty \cdot [1 - e^{-kt}]$$

where $A_t$ is the percentage of drug released from the multiparticulates at time t, $A_\infty$ is the percentage of drug released from the multiparticulates over long periods times, equal in this case to the amount released at the end of the dissolution test plus the residual amount in the multiparticulates, t is the time in minutes, and k is the drug release rate constant in $min^{-1}$.

Drug Release Rate in GB

The drug release rate from the multiparticulates in a simulated GB solution was determined as described above, except that the GB dissolution media consisted of 750 mL of 0.01 N HCl. Samples were collected at various time points following addition of the multiparticulates to the flask and analyzed for drug, residual drug remaining in the multiparticulates was determined and the dissolution rate constant in GB was calculated, all as described above.

Example 1

Multiparticulates MP2 were post-treated as follows. Samples of the multiparticulates were placed in a shallow tray at a depth of about 2 cm. This tray was then placed in a controlled-atmosphere oven at 40° C. and 75% RH for 5 days. The post-treated multiparticulates were analyzed by PXRD and 96%±11% of the azithromycin in the multiparticulates was determined to be in the crystalline dihydrate form. Thus, the post-treatment process resulted in a relative degree of improvement in crystallinity of 5.8 ((1-0.77)÷(1-0.96)).

The rate of azithromycin dissolution from the post-treated multiparticulates was determined using a dissolution medium of IB, with the results presented in Table 1. The dissolution rate constant in IB was calculated and is given in Table 2.

Samples of the post-treated multiparticulates of Example 1 were sealed in packets as described for Control C1 and placed in a controlled-atmosphere oven set at 40° C./75% RH for 18 weeks. The samples were then removed from the packets and the rate of azithromycin release from the multiparticulates was measured as described above. The results of these tests, given in Tables 1 and 2, show that the dissolution rate constant for the multiparticulates stored for 18 weeks at 40° C. and 75% RH (0.017 $min^{-1}$) was identical to that of the post-treated multiparticulates before storage. Thus, the change in dissolution performance was essentially nil.

TABLE 1

| | Post-treated 5 Days at 40° C./75% RH | |
| --- | --- | --- |
| Example 1 | Time (min) | Azithromycin Released (%) |
| Initial | 0 | 0 |
| | 5 | 1 |
| | 15 | 4 |
| | 30 | 9 |
| | 60 | 18 |
| | 120 | 36 |
| | 180 | 48 |

TABLE 1-continued

Post-treated 5 Days at 40° C./75% RH

| Example 1 | Time (min) | Azithromycin Released (%) |
|---|---|---|
| After 18 weeks | 0 | 0 |
| | 5 | 1 |
| | 15 | 4 |
| | 30 | 9 |
| | 60 | 18 |
| | 120 | 37 |
| | 180 | 51 |

TABLE 2

| Example | Azithromycin Released at 180 min (%) | Residual Azithromycin (%) | $A_\infty$ (%) | Dissolution Rate Constant in IB (min$^{-1}$) |
|---|---|---|---|---|
| 1 (initial) | 97 | 3 | 100 | 0.017 |
| 1 (after 18 weeks) | 95 | 3 | 98 | 0.017 |

Example 2

Multiparticulates MP3 were post-treated as described in Example 1 except that the treatment was for 7 days. The rate of azithromycin release from the so post-treated multiparticulates was determined in IB, with the results presented in Table 3. The dissolution rate constant in IB was calculated from these data and is given in Table 4.

Samples of the post-treated multiparticulates of Example 2 were sealed in packets as in Control C1 and placed in a controlled atmosphere oven set at 40° C./75% RH for 3 weeks. The samples were then removed from the packets and the rate of azithromycin release from the multiparticulates was measured as described above. The results of these tests, given in Tables 3 and 4, show that the dissolution rate constant for the multiparticulates stored for 3 weeks at 40° C. and 75% RH (0.016 min$^{-1}$) was identical to that of the post-treated multiparticulates before storage. Thus, the change in dissolution rate was essentially nil.

TABLE 3

| Example 2 | Time (min) | Azithromycin Released (%) |
|---|---|---|
| Initial | 0 | 0 |
| | 5 | 6 |
| | 15 | 18 |
| | 30 | 36 |
| | 60 | 58 |
| | 120 | 85 |
| | 180 | 95 |
| After 3 weeks | 0 | 0 |
| | 5 | 6 |
| | 15 | 19 |
| | 30 | 37 |
| | 60 | 59 |
| | 120 | 83 |
| | 180 | 93 |

TABLE 4

| Example | Azithromycin Released at 180 min (%) | Residual Azithromycin (%) | $A_\infty$ (%) | Dissolution Rate Constant in IB (min$^{-1}$) |
|---|---|---|---|---|
| 2 (initial) | 95 | 5 | 100 | 0.016 |
| 2 (after 3 weeks) | 93 | 4 | 97 | 0.016 |

Example 3

Multiparticulates MP4 were post-treated as described in Example 1 except that the multiparticulates were post-treated for 2 days at 45° C./60% RH. The post-treated multiparticulates were analyzed by PXRD and 98%±5% of the azithromycin in the multiparticulates was found to be in the crystalline dihydrate form. Thus, the post-treatment process resulted in an increase in the percent crystallinity of drug in the multiparticulates. The relative degree of improvement in crystallinity of improvement in crystallinity was 14.

The rate of azithromycin release from the so post-treated multiparticulates was determined in IB, with the results presented in Table 5. The dissolution rate constant in IB was calculated is given in Table 6.

Samples of the post-treated multiparticulates of Example 3 were sealed in packets as Control C1 and placed in a controlled atmosphere oven set at 40° C./75% RH for six weeks. The samples are then removed from the packets and the rate of azithromycin release from the multiparticulates was measured as described above. The results of these tests, given in Tables 5 and 6, show that the dissolution rate constant for the multiparticulates stirred for 6 weeks at 40° C. and 75% RH (0.016 min$^{-1}$) was 89% of the dissolution rate constant of the post-treated multiparticulates before storage (0.018 min$^{-1}$), resulting in a change in dissolution rate of 11%.

TABLE 5

| Example 3 | Time (min) | Azithromycin Released (%) |
|---|---|---|
| Initial | 0 | 0 |
| | 5 | 7 |
| | 15 | 23 |
| | 30 | 42 |
| | 60 | 66 |
| | 120 | 92 |
| | 180 | 100 |
| After 6 weeks | 0 | 0 |
| | 5 | 7 |
| | 15 | 23 |
| | 30 | 39 |
| | 60 | 59 |
| | 120 | 83 |
| | 180 | 96 |

TABLE 6

| Example 3 | Azithromycin Released at 180 min (%) | Residual Azithromycin (%) | $A_\infty$ (%) | Dissolution Rate Constant in IB (min$^{-1}$) |
|---|---|---|---|---|
| Initial | 100 | 2 | 102 | 0.018 |
| After 6 weeks | 96 | 3 | 99 | 0.016 |

Example 4

Multiparticulates MP5 were post-treated as described in Example 1. The post-treated multiparticulates were analyzed by PXRD and 99+%±4% of the azithromycin in the multiparticulates was determined to be in the crystalline dihydrate form. Thus, the post-treatment process resulted in an increase in the percent crystallinity of the drug, corresponding to a relative degree of improvement in crystallinity of at least 16.

The rate a azithromycin release from the post-treated multiparticulates was determined in IB, with the results presented in Table 7. The dissolution rate constant in IB was calculated and is give in Table 8.

Samples of the post-treated multiparticulates of Example 4 were sealed in packets as in control C1 and placed in a controlled atmosphere oven set at 40° C./75% RH for three weeks. The samples were then removed from the packets and the rate of azithromycin release from the multiparticulates was measured as described above. The results of these tests, given in Tables 7 and 8, show that the dissolution rate constant for the multiparticulates stored for 3 weeks at 40° C. and 75% RH (0.025 min$^{-1}$) was identical to that of the post-treated multiparticulates before storage, resulting in a change in dissolution performance of essentially nil.

TABLE 7

| Example 4 | Time (min) | Azithromycin Released (%) |
|---|---|---|
| Initial | 0 | 0 |
|  | 5 | 15 |
|  | 15 | 33 |
|  | 30 | 51 |
|  | 60 | 74 |
|  | 120 | 93 |
|  | 180 | 97 |
| After 3 weeks | 0 | 0 |
|  | 5 | 11 |
|  | 15 | 32 |
|  | 30 | 53 |
|  | 60 | 79 |
|  | 120 | 96 |
|  | 180 | 99 |

TABLE 8

| Example 4 | Azithromycin Released at 180 min (%) | Residual Azithromycin (%) | $A_\infty$ (%) | Dissolution Rate Constant in IB (min$^{-1}$) |
|---|---|---|---|---|
| Initial | 97 | 2 | 99 | 0.025 |
| After 3 weeks | 99 | 1 | 100 | 0.025 |

Example 5

Multiparticulates MP6 were post-treated as described in Example 1. The post-treated multiparticulates were analyzed by PXRD and 86%±3% of the azithromycin in the multiparticulates was found to be in the crystalline dihydrate form. Thus, the post-treatment process resulted in an increase in the crystallinity of drug in the multiparticulates, corresponding to a relative degree of improvement in crystallinity of 2.6.

The rate of azithromycin release from the post-treated multiparticulates was determined in IB, with the results presented in Table 9. The dissolution rate constant in IB was calculated and is given in Table 10.

Samples of the post-treated multiparticulates of Example 5 were sealed in packets as in Control C1 and placed in a controlled atmosphere oven set at 40° C./75% RH for 12 weeks. The samples were then removed from the packets and the rate of azithromycin release from the multiparticulates was measured as described above. The results of these tests, given in Tables 9 and 10, show that the dissolution rate constant for the multiparticulates stored for 12 weeks at 40° C. and 75% RH (0.019 min$^{-1}$) was 95% that of the post-treated multiparticulates before storage (0.020 min$^{-1}$), resulting in a change in dissolution performance of 5%.

TABLE 9

| Example 5 | Time (min) | Azithromycin Released (%) |
|---|---|---|
| Initial | 0 | 0 |
|  | 5 | 9 |
|  | 15 | 25 |
|  | 30 | 44 |
|  | 60 | 68 |
|  | 120 | 88 |
|  | 180 | 95 |
| After 12 weeks | 0 | 0 |
|  | 5 | 7 |
|  | 15 | 23 |
|  | 30 | 41 |
|  | 60 | 65 |
|  | 120 | 90 |
|  | 180 | 95 |

TABLE 10

| Example 5 | Azithromycin Released at 180 min (%) | Residual Azithromycin (%) | $A_\infty$ (%) | Dissolution Rate Constant in IB (min$^{-1}$) |
|---|---|---|---|---|
| Initial | 95 | 2 | 97 | 0.020 |
| After 12 weeks | 95 | 2 | 97 | 0.019 |

Examples 6-15

Multiparticulates MP3 were post-treated using the 10 different sets of conditions shown in Table 11 and the rates of azithromycin release from the post-treated multiparticulates were determined in IB. The dissolution rate constants in IB were then calculated and the results are summarized in Table 11. These data show that the lower the post-treatment temperature, the longer the post-treatment should be to obtain multiparticulates with a stable azithromycin release rate.

TABLE 11

| Example | Temperature (° C.) | Relative Humidity (%) | Time (days) | Dissolution Rate Rate Constant in IB (min⁻¹) |
|---|---|---|---|---|
| 6 | 30 | 11 | 14 | 0.017 |
|   |    |    | 21 | 0.015 |
|   |    |    | 42 | 0.018 |
|   |    |    | 84 | 0.017 |
| 7 | 40 | 11 | 2  | 0.024 |
|   |    |    | 14 | 0.030 |
|   |    |    | 21 | 0.030 |
|   |    |    | 84 | 0.029 |
| 8 | 50 | 11 | 0.5 | 0.049 |
|   |    |    | 0.75 | 0.045 |
|   |    |    | 1  | 0.047 |
|   |    |    | 2  | 0.049 |
|   |    |    | 3  | 0.049 |
| 9 | 30 | 52 | 7  | 0.019 |
|   |    |    | 14 | 0.019 |
|   |    |    | 21 | 0.018 |
|   |    |    | 42 | 0.021 |
|   |    |    | 84 | 0.028 |
| 10 | 40 | 48 | 2  | 0.035 |
|   |    |    | 14 | 0.061 |
|   |    |    | 42 | 0.062 |
| 11 | 50 | 46 | 0.5 | 0.063 |
|   |    |    | 0.75 | 0.069 |
|   |    |    | 1  | 0.059 |
|   |    |    | 2  | 0.065 |
| 12 | 30 | 80 | 7  | 0.018 |
|   |    |    | 14 | 0.023 |
|   |    |    | 21 | 0.023 |
|   |    |    | 42 | 0.031 |
|   |    |    | 84 | 0.036 |
| 13 | 40 | 80 | 1  | 0.031 |
|   |    |    | 3  | 0.057 |
|   |    |    | 5  | 0.061 |
|   |    |    | 7  | 0.063 |
| 14 | 45 | 79 | 0.5 | 0.048 |
|   |    |    | 0.75 | 0.047 |
|   |    |    | 1  | 0.057 |
|   |    |    | 1.5 | 0.052 |
|   |    |    | 2  | 0.055 |
| 15 | 50 | 79 | 0.05 | 0.038 |
|   |    |    | 0.08 | 0.052 |
|   |    |    | 0.17 | 0.055 |
|   |    |    | 0.25 | 0.060 |
|   |    |    | 0.75 | 0.070 |
|   |    |    | 1  | 0.063 |
|   |    |    | 2  | 0.064 |

Example 16

Multiparticulates MP1 were post-treated by placing them in a controlled atmosphere chamber held at 47° C. and 70% RH for the times shown in Table 12. The rate of azithromycin release from the post-treated multiparticulates was determined in IB, and the dissolution rate constants in IB were then calculated for all time intervals except at 4 and 8 hours. The results are summarized in Table 12.

The post-treated multiparticulates were also analyzed by PXRD to determine the crystallinity of the azithromycin in the multiparticulates. These data, also shown in Table 12, indicate that the degree of crystallinity of the azithromycin increased with post-treatment time, reaching 99+% crystalline dihydrate after about 18 hours of post-treatment.

TABLE 12

| Post-treatment Time (hrs) | Dissolution Rate Constant in IB (min⁻¹) | Crystallinity of Azithromycin (%) |
|---|---|---|
| 0 (no post-treatment) | 0.003 | ND |
| 1  | 0.008 | 81 |
| 2  | 0.011 | 79 |
| 3  | 0.012 | 87 |
| 4  | ND    | 98 |
| 6  | 0.015 | ND |
| 8  | ND    | 96 |
| 12 | 0.017 | ND |
| 18 | 0.017 | 99+ |
| 24 | 0.017 | 99+ |

ND = not determined

Example 17

Multiparticulates MP1 were post-treated by placing them in a tray to a depth of 10 cm, and then placing the tray into a controlled atmosphere chamber held at 47° C. and 70% RH for 24 hours. Following post-treatment, samples of the post-treated multiparticulates were obtained from the top, middle, and bottom of the tray, corresponding to depths of 0-2 cm, 4-6 cm, and 8-10 cm, respectively. The rate of azithromycin release from the post-treated multiparticulates was then determined in IB, and the dissolution rate constants in IB were calculated. The results, summarized in Table 13, show that the performance of the post-treated multiparticulates was virtually the same regardless of the sampling depth.

TABLE 13

| Sampling Depth (cm) | Dissolution Rate Constant in IB (min⁻¹) |
|---|---|
| 0–2  | 0.018 |
| 4–6  | 0.019 |
| 8–10 | 0.018 |

Examples 18-22

Multiparticulates MP4 were post-treated by placing them in a controlled-atmosphere chamber at the conditions shown in Table 14. The rate of azithromycin release from the post-treated multiparticulates was determined in IB, and the dissolution rate constants were calculated. The results are summarized in Table 14.

The post-treated multiparticulates were also analyzed by PXRD to determine the crystallinity of the azithromycin in the multiparticulates. These data, also shown in Table 14, indicate that the degree of dihydrate crystallinity of the azithromycin increased with post-treatment time, reaching at least 97% within the post-treatment times studied. Thus, the post-treatment process resulted in a relative degree of improvement in crystallinity of at least 9.3 for all conditions studied.

TABLE 14

| Example | Temperature (°C.) | Relative Humidity (%) | Time (hr) | Dissolution Rate Constant in IB (min$^{-1}$) | Azithromycin Crystallinity (%) |
|---|---|---|---|---|---|
| MP4 (untreated) | NA | NA | NA | — | 72 |
| 18 | 45 | 60 | 18 | 0.018 | 97 |
|  |  |  | 24 | 0.018 | 99+ |
|  |  |  | 48 | 0.018 | 98 |
| 19 | 45 | 80 | 18 | 0.017 | 93 |
|  |  |  | 24 | 0.017 | 96 |
|  |  |  | 48 | 0.016 | 98 |
| 20 | 49 | 60 | 18 | 0.019 | 93 |
|  |  |  | 24 | 0.017 | 97 |
|  |  |  | 48 | 0.016 | 98 |
| 21 | 49 | 80 | 18 | 0.016 | 89 |
|  |  |  | 24 | 0.016 | 96 |
|  |  |  | 48 | 0.015 | 99+ |
| 22 | 47 | 70 | 18 | 0.017 | 97 |
|  |  |  | 24 | 0.017 | 97 |
|  |  |  | 48 | 0.016 | 97 |

NA = not applicable

Control C1

The dissolution stability of Multiparticulates MP7 was determined by sealing samples of the multiparticulates in conventional pharmaceutical foil/polymer/foil packets and placing them in a controlled atmosphere oven set at 40° C./75% RH for three weeks. The samples were removed from the packets and the rate of azithromycin release from the multiparticulates was measured in GB as described above except that data points were also collected at 120 minutes and 180 minutes. The results of this test are given in Tables 15.

The dissolution rate constant in GB was then calculated as described above, and the results are reported in Table 16. The data show that for untreated Multiparticulates MP7, the dissolution rate constant (0.074 min$^{-1}$) after storage for three weeks at 40° C./75% RH was almost 2.6-fold the dissolution rate constant (0.028 min$^{-1}$) prior to storage, resulting in a change in dissolution performance of 260% for the non-post-treated multiparticulates.

TABLE 15

| Multiparticulates | Time (min) | Azithromycin Released (%) |
|---|---|---|
| MP7 | 0 | 0 |
|  | 5 | 7 |
|  | 15 | 25 |
|  | 30 | 45 |
|  | 60 | 73 |
| MP7 After 3 weeks at 40° C./75% RH | 0 | 0 |
|  | 5 | 22 |
|  | 15 | 65 |
|  | 30 | 87 |
|  | 60 | 92 |

TABLE 16

| Multiparticulates | Azithromycin Released at 60 min (%) | Residual Azithromycin (%) | A$_\infty$ (%) | Dissolution Rate Constant in GB (min$^{-1}$) |
|---|---|---|---|---|
| MP7 Before Storage | 73 | 8 | 81 | 0.028 |
| MP7 After 3 weeks at 40° C./75% RH | 92 | 1 | 88 | 0.074 |

Example 23

Multiparticulates MP10 were post-treated by placing them in a tray at a depth of about 2 cm and the tray placed in a controlled atmosphere oven at 40° C. and 75% RH for 5 days. Samples of the post-treated multiparticulates were analyzed by PXRD and 99+%±6% of the azithromycin in the multiparticulates was in the form of the crystalline dihydrate. Thus, the post-treatment process increased the crystallinity of the drug in the multiparticulate, resulting in a relative degree of improvement in crystallinity of at least 6([1-0.94]+[1-0.99]).

The rate of release of azithromycin from the post-treated multiparticulates of Example 23 was determined in IB and the results are reported in Table 17. The dissolution rate constant in IB was calculated and is reported in Table 18.

TABLE 17

| Example No. | Time (min) | Azithromycin Released (%) |
|---|---|---|
| 23 | 0 | 0 |
|  | 15 | 14 |
|  | 30 | 27 |
|  | 60 | 44 |
|  | 120 | 68 |
|  | 180 | 81 |
| 23 After 12 weeks at 40° C./75% RH | 0 | 0 |
|  | 15 | 14 |
|  | 30 | 25 |
|  | 60 | 41 |
|  | 120 | 63 |
|  | 180 | 76 |

Samples of the post-treated multiparticulates of Example 23 were sealed in packets as in Control C1 and placed in a controlled atmosphere oven set at 40° C./75% RH for 12 weeks. The samples were then removed from the packets and the rate of azithromycin release from the multiparticulates was measured as described above. The results are also reported in Table 17.

These results show that the dissolution performance of the post-treated multiparticulates of Example 23 was virtually the same after storage for 12 weeks at prior to storage, indicating that the post-treatment process stabilized the dissolution performance.

TABLE 18

| Example No. | Formulation (Azithromycin/ COMPRITOL 888 ATO/ PLURONIC F127, wt %) | k (1/min) |
|---|---|---|
| 23 | 50/47/3 | 0.010 |
| 23 after 12 weeks at 40° C./75% RH | 50/47/3 | 0.010 |

Example 24

Multiparticulates MP11 were post-treated as follows. Samples of the multiparticulates were placed in sealed barrels. The barrels were then placed in a controlled atmosphere chamber at 40° C. for 3 weeks.

The rate of release of azithromycin from these post-treated multiparticulates was determined using the following procedure. Approximately 4 g of the multiparticulates (containing about 2000 mgA of the drug) were placed into a 125 mL bottle containing approximately 21 g of a dosing vehicle consisting of 93 wt % sucrose, 1.7 wt % trisodium phosphate, 1.2 wt % magnesium hydroxide, 0.3 wt % hydroxypropyl cellulose, 0.3 wt % xanthan gum, 0.5 wt % colloidal silicon dioxide, 1.9 wt % titanium dioxide, 0.7 wt % cherry flavoring, and 1.1 wt % banana flavoring. Next, 60 mL of purified water was added and the bottle was shaken for 30 seconds. The contents were added to a USP Type 2 dissoette flask equipped with Teflon-coated paddles rotating at 50 rpm. The flask contained 840 mL of 100 mM $Na_2HPO_4$ buffer, pH 6.0, held at 37.0±0.5° C. The bottle was rinsed twice with 20 mL of the buffer from the flask, and the rinse was returned to the flask to make up a final volume of 900 mL. A 3-mL sample of the fluid in the flask was then collected at 15, 30, 60, 120, and 180 minutes following addition of the multiparticulates to the flask. The samples were filtered using a 0.45-μm syringe filter prior to analyzing via HPLC (Hewlett Packard 1100, Waters Symmetry $C_8$ column, 45:30:25 acetonitrile:methanol:25 mM $KH_2PO_4$ buffer at 1.0 mL/min, absorbance measured at 210 nm with a diode array spectrophotometer). The results of this dissolution test are reported in Table 19.

TABLE 19

| Example No. | Time (min) | Azithromycin Released (%) |
|---|---|---|
| 24 post-treated | 0 | 0 |
| | 15 | 28 |
| | 30 | 48 |
| | 60 | 74 |
| | 120 | 94 |
| | 180 | 98 |

Example 25

Multiparticulates MP12 were post-treated as follows. Prior to treatment, 81 wt % of the drug in the multiparticulates was in the crystalline dihydrate form. The multiparticulates contained water, a mobility-enhancing agent, which had been injected into the extruder used to form the multiparticulates. Samples of the multiparticulates were placed in sealed barrels. The barrels were then placed in a controlled atmosphere chamber at 40° C. for 10 days. Samples of the post-treated multiparticulates were evaluated by PXRD, which showed that after post-treatment about 99 wt % of the azithromycin in the multiparticulates was in the crystalline dihydrate form. Thus, the use of a mobility-enhancing agent in the course of forming the multiparticulates coupled with an elevated temperature post-treatment, resulted in a substantial increase in the crystallinity of the azithromycin in the multiparticulate.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. A process for making drug-containing multiparticulates comprising the steps:
   (a) forming multiparticulates comprising a drug, a pharmaceutically acceptable carrier, and an poloxamer, said carrier having a melting point of $T_m°$ C.; and
   (b) treating said multiparticulates of step (a) by at least one of (i) heating said multiparticulates to a temperature of at least 35° C. and less than ($T_m°$ C. minus 10° C.), and (ii) exposing said multiparticulates to a mobility enhancing agent, to form a post-treated multiparticulate;
wherein step (b) is conducted for a period of time sufficient to achieve a degree of crystallinity of said drug in said multiparticulates that is greater than the crystallinity of said drug in a control composition consisting essentially of the untreated multiparticulates of step (a) and wherein said carrier is a mixture of glyceryl mono-, di-, and tribehenates.

2. The process of claim 1 wherein said multiparticulates of step (a) are treated by exposing them to a mobility-enhancing agent to form a post-treated multiparticulate.

3. The process of claim 1 wherein said multiparticulates are treated to a temperature of at least 35° C. and less than (Tm° C. minus 10° C.).

4. The process of claim 1 wherein said drug in said post-treated multiparticulate has an improvement in stability relative to said drug in said control composition.

5. The process of claim 4 wherein said improvement in stability comprises a relative degree of improvement in drug crystal form of at least 1.25 relative to said control composition.

6. The process of claim 4 wherein said improvement in stability comprises an improvement in dissolution performance of at least 1.25 relative to said control composition.

7. The process of claim 4 wherein said improvement in stability comprises an improvement in chemical stability of at least 1.25 relative to said control composition.

8. The process of claim 1 wherein step (b) comprises both heating said multiparticulates and exposing said multiparticulates to said mobility-enhancing agent.

9. The process of claim 1 wherein said mobility enhancing agent is selected from the group consisting of water, methanol, ethanol, propanol and its isomers, butanol and its isomers, acetone, methyl ethyl ketone, methyl iso-butyl ketone, ethyl acetate, tetrahydrofuran, acetonitrile, cyclohexane, formic acid, acetic acid and mixtures thereof.

10. The process of claim 9 wherein said mobility-enhancing agent is water in the form of water vapor comprising greater than about 10% relative humidity.

11. The process of claim 1 wherein step (b) comprises heating said multiparticulates at a temperature of 40° to 50° C. in an atmosphere of at least 50% relative humidity for 30 days or less.

12. The process of claim 3 wherein step (b) comprises (i) placing said multiparticulates in a sealed container; and (ii) heating said sealed container at a temperature of not more than ($T_m°$ minus 10° C.) for a time sufficient to achieve a degree of drug crystallinity of at least 95%.

13. The process of claim 3 wherein step (a) comprises (i) forming a preblend feed comprising said drug, said carrier and said mobility-enhancing agent; (ii) forming a molten mixture of said preblend feed in an extruder; (iii) delivering said molten mixture to atomizing means to form droplets from said mixture; and (iv) congealing said droplets to form said multiparticulates.

14. The process of claim 3 wherein step (a) comprises (i) forming in an extruder a first molten mixture comprising said drug and said carrier; (ii) delivering said mobility-enhancing agent to said extruder to form a second molten mixture comprising said drug, said carrier and said mobility-enhancing agent; (iii) delivering said second molten mixture to atomizing means to form droplets; and (iv) congealing said droplets to form said multiparticulates.

15. The process of claim 14 wherein step (b) comprises (i) placing said multiparticulates in a sealed container; and (ii) heating said sealed container at a temperature of not more than: ($Tm°$ minus 10° C.) for a time sufficient to achieve a degree of drug crystallinity of at least 95%.

16. The process of claim 15 wherein said sealed container is heated at a temperature of from 40° to 50° C. for about 5 to about 21 days.

17. The process of claim 15 wherein said mobility-enhancing agent is water.

18. The process of claim 17 wherein said water is in a form selected from a liquid and a vapor.

19. The process of claim 1 wherein said drug is selected from azithromycin dihydrate and pharmaceutically acceptable forms thereof.

* * * * *